US005642625A

United States Patent [19]
Cates, Jr. et al.

[11] Patent Number: 5,642,625
[45] Date of Patent: Jul. 1, 1997

[54] HIGH VOLUME HYPERPOLARIZER FOR SPIN-POLARIZED NOBLE GAS

[75] Inventors: Gordon D. Cates, Jr., Skillman, N.J.; Bastiaan Driehuys, Bristol, Pa.; William Happer, Princeton, N.J.; Hunter Middleton, Princeton, N.J.; Eli Miron, Princeton, N.J.; Brian Saam, Princeton, N.J.; Daniel Walter, Chicago, Ill.

[73] Assignee: The Trustees of Princeton University, Princeton, N.J.

[21] Appl. No.: 622,863

[22] Filed: Mar. 29, 1996

[51] Int. Cl.$^6$ .................................................. B01D 8/00
[52] U.S. Cl. ............................... 62/55.5; 62/919; 62/925
[58] Field of Search .......................... 62/55.5, 919, 925, 62/637; 372/56

[56] References Cited

U.S. PATENT DOCUMENTS

| | | | |
|---|---|---|---|
| 4,977,749 | 12/1990 | Sercel | 62/55.5 |
| 5,073,896 | 12/1991 | Reid et al. | 62/55.5 |

OTHER PUBLICATIONS

Wagshul, et al., "Optical Pumping Of High-Density Rb With A Broadband Dye Laser And GaAl As Siode Laser Arrays: Application to $^3$He Polarization", *Physical Review A*, vol. 40, No. 8, pp. 4447-4454 (1989).

Gatzke, et al., "Extraordinarily Slow Nuclear Spin Relaxation In Frozen Laser-Polarized $^{129}$Xe", *Physical Review Letters*, vol. 50, No. 5, pp. 690-693 (1993).

Cates, et al., "Laser Production Of Large Nuclear-Spin Polarization In Frozen Xenon", *Physical Review Letters*, vol. 65, No. 20, pp. 2591-2594 (1990).

Becker, et al., "Study Of Mechanical Compression Of Spin-Polarized $^3$He Gas", *Nuclear Instruments And Methods In Physics Research*, vol. A 346, pp. 45-51 (1994).

Middleton, et al., "MR Imaging With Hyperpolarized $^3$He Gas", *Magnetic Resonance In Medicine*, vol. 33, pp. 271-275 (1995).

Cummings, et al., "Optical Pumping Of Rb Vapor Using High-Power $Ga_{1-x}Al_xAs$ Diode Laser Arrays", *Physical Review A*, vol. 51, No. 6, pp. 4842-4851 (1995).

Middleton, "The Spin Structure Of The Neutron Determined Using A Polarized $^3$He Target", *Ph.D Dissertation, Princeton University* (1994).

*Primary Examiner*—Ronald C. Capossela
*Attorney, Agent, or Firm*—Hoffmann & Baron

[57] ABSTRACT

A method and apparatus for hyperpolarization of flowing noble gases is disclosed, including means for hyperpolarization of noble gases in a continuous flow arrangement. Noble gases such as xenon-129 and helium-3 can be hyperpolarized using the disclosed method and apparatus. Preferably, the noble gas is hyperpolarized via spin exchange between atoms of the noble gas and an alkali metal such as rubidium. Also, a method and apparatus for accumulation and/or storage of hyperpolarized noble gases in a continuous flow arrangement is provided. The method and apparatus enable large scale production, storage, and usage of hyperpolarized noble gases for numerous purposes, including imaging of human and animal subjects through magnetic resonance imaging (MRI) techniques.

62 Claims, 6 Drawing Sheets

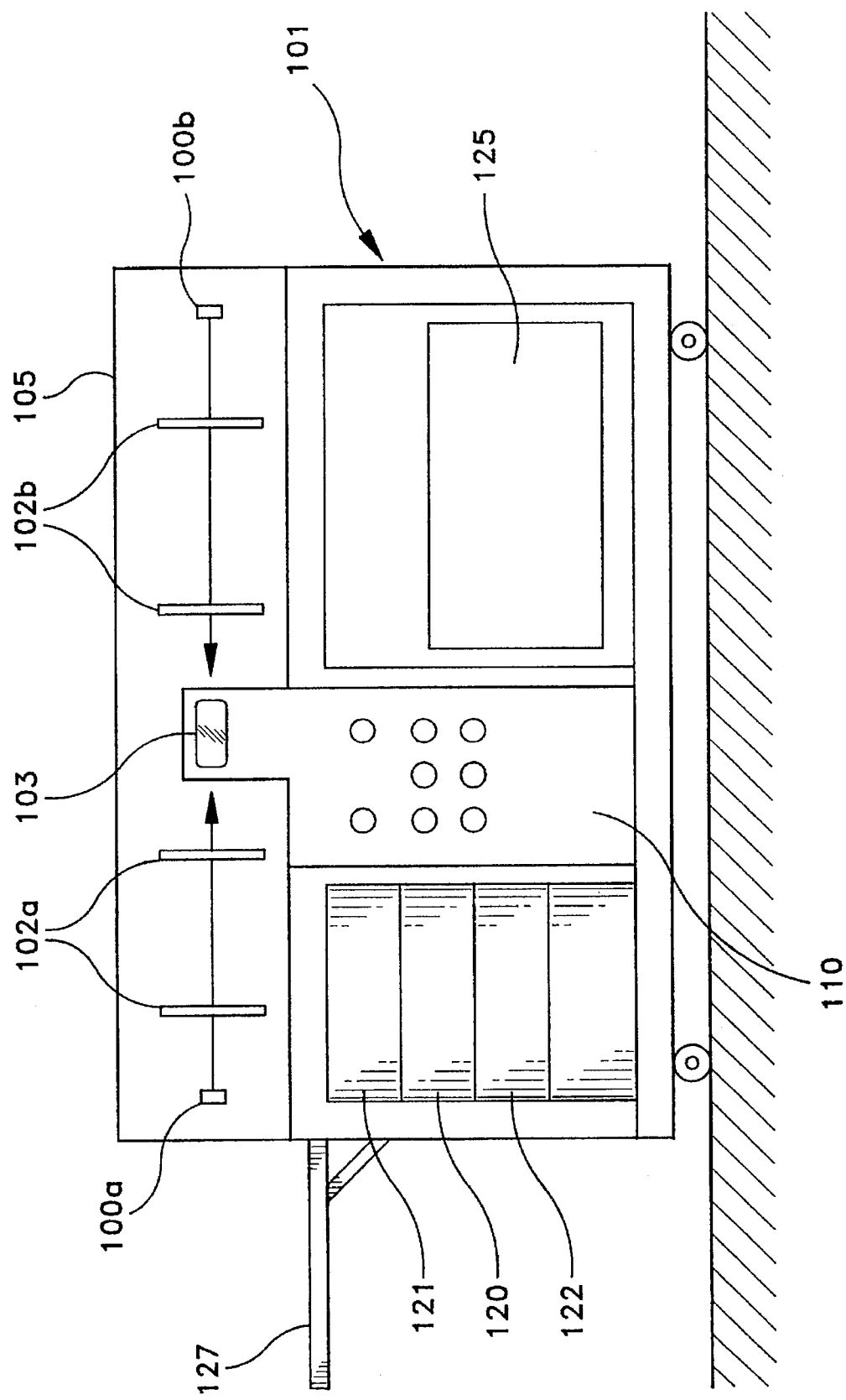

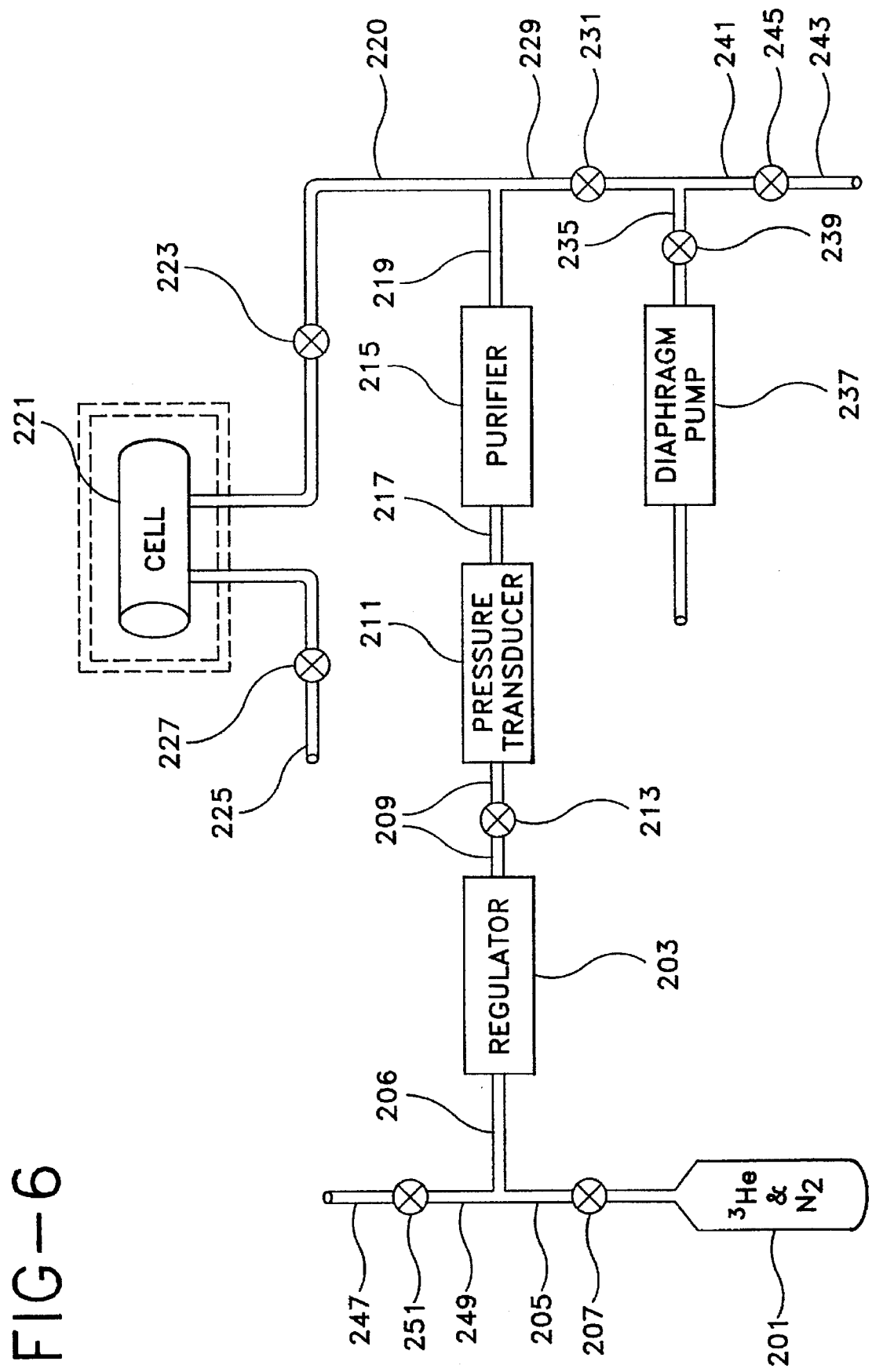

HIGH VOLUME HYPERPOLARIZER FOR SPIN-POLARIZED NOBLE GAS

This invention was made with Government support under Grant Nos. DAAH04-94-G-0204, DAMD1794J4469, and F49620-94-0466. The Government may have fights in this invention.

BACKGROUND OF THE INVENTION

The invention relates to apparatus and methods for hyperpolarizing noble gases. Specifically, the invention relates to methods and apparatus for producing significant quantities of hyperpolarized noble gases in a continuous manner.

Nuclear magnetic resonance (NMR) is a phenomenon which can be induced through the application of energy against an atomic nucleus being held in a magnetic field. The nucleus, if it has a magnetic moment, can be aligned within an externally applied magnetic field. This alignment can then be transiently disturbed by application of a short burst of radio frequency energy to the system. The resulting disturbance of the nucleus manifests as a measurable resonance or wobble of the nucleus relative to the external field.

For any nucleus to interact with an external field, however, the nucleus must have a magnetic moment, i.e., non-zero spin. Experimental nuclear magnetic resonance techniques are, therefore, limited to study of those target samples which include a significant proportion of nuclei exhibiting non-zero spin. A highly preferred such nucleus is the proton $^1H$), which is typically studied by observing and manipulating the behavior of water protons ($^1H_2O$) in magnetic fields. Other nuclei, including certain noble gas nuclei such as $^3He$ and $^{129}Xe$, are in principle suited to study via NMR. However, the low relative natural abundance of these isotopes, their small magnetic moments, and other physical factors have made NMR study of these nuclei difficult if not impossible to accomplish.

One important consideration in studying noble gas nuclei via NMR is that they normally yield only a very low NMR signal intensity. It is known, however, that the spin polarization of such noble gases as $^3He$ and $^{129}Xe$ can be increased over natural levels, i.e., populations of these isotopes can be artificially "hyperpolarized", to provide a much larger NMR signal. One preferred hyperpolarization technique is known as spin exchange hyperpolarization. Without describing this technique in exhaustive detail, in this scenario a noble gas is hyperpolarized via interaction with an alkali-metal vapor, such as rubidium, which itself has been polarized by absorption of laser energy of an appropriate wavelength. The polarized rubidium transfers its polarization to the noble gas through a phenomenon known as spin exchange transfer. The end result is that the noble gas becomes "hyperpolarized", i.e., more polarized than it would otherwise be. Details of the theory underlying the spin exchange hyperpolarization technique are available in the literature.

While well established as a theoretical phenomenon, the actual practice of spin exchange hyperpolarization has proven to be something of an art. The production and handling of hyperpolarized noble gases is not only logistically difficult, it is expensive as well. Moreover, due to the experimental nature of spin exchange studies, the production of hyperpolarized noble gases has typically been undertaken only on a small scale. Exquisite craftsmanship is typically required, involving expertise in a variety of fields including lasers, electronics, glass-blowing, ultra-high vacuum pump operation, high-purity gas handling as well as nuclear magnetic resonance spectroscopy.

For example, the production of a single sample of hyperpolarized noble gas has typically involved the fabrication of a single-use sealed glass cell with a volume capacity of only a few tens to a few hundred cubic centimeters. Such cells have required delicacy in manufacture, yet their quality, as measured by their tendency to depolarize the noble gas, has not always been predictable. Moreover, use of such cells for spin exchange requires that they be sealed with the alkali metal present therein. This has meant that care must be taken to remove impurities which can cause oxidation of the metal and consequent ruination of the cell. Other problems arise in the glass itself which can depolarize the noble gas faster than it can be polarized. For study of polarized noble gas by nuclear magnetic resonance (NMR) techniques, the sealed cell must be opened or destroyed to release the hyperpolarized gas into the NMR spectrometer. Proceeding to the next sample has required repeating all of these steps, including fabricating and filling a new glass cell, which might or might not have similar qualities, resulting in a tedious and often unpredictable procedure.

Middleton established for the first time the possibility of making sealed cells capable of containing larger quantities of a noble gas for hyperpolarization by the spin exchange technique. Middleton H., *The Spin Structure of the Neutron Determined Using a Polarized $^3He$ Target*, Ph.D. Dissertation, Princeton University, (1994). Even so, the reliability of the procedures described in this publication has not proven to be suited to routine use, in that sample-to-sample variability has remained a problem. Moreover, there is no disclosure in this document of any method of making refillable cells or cells which could be used on a continuous or flowing basis without significant rehabilitation. Accordingly, while progress in cell manufacture has occurred, the art has not provided means for making refillable or continuous flow spin exchange pumping cells.

A publication by Becker et al., *Nucl. Inst. & Meth. in Phys. Res. A*, 346:45–51 (1994) describes a method for producing hyperpolarized $^3He$ by a distinctly different polarization method known as metastability exchange. This approach requires the use of extremely low pressures of $^3He$, i.e., about 0.001 atm to about 0.01 atm, and does not involve the use of an alkali metal. Significant accumulation of hyperpolarized gas is limited by the necessity of using huge pumping cells (i.e., about 1 meter long) and then compressing the gas to a useful level. The Becker et al. publication discloses an ingenious but technically difficult approach which employs large volume compressors made of titanium for compressing the gas to about atmospheric pressure. Unfortunately, manufacture and operation of such a system requires great engineering skill, limiting the reproducibility and operability of the system on a routine basis. The apparatus described by Becker et al. also requires significant amounts of floor space and cannot be moved. The Becker et al. paper also avoids the use of alkali metals in the pumping cells, and does not disclose any method of producing hyperpolarized noble gas by spin exchange. Hence, the Becker et al. paper does not resolve the complexity of manufacturing pumping cells in which an alkali metal is employed. As a result, this publication does not describe or suggest any method or apparatus related to the production and delivery of arbitrarily large or small quantities of hyperpolarized noble gas by spin exchange.

It was recently demonstrated that hyperpolarized noble gases can be imaged by nuclear magnetic resonance imaging (MRI) techniques. See U.S. patent application Ser. No. 08/225,243. In addition, because the noble gases as a group are inert and non-toxic, it was found that hyperpolarized noble gases can be used for MRI of human and animal subjects. As a result, there exists a growing need for the generation of larger quantities of hyperpolarized noble gases. Moreover, because of medical and veterinary concerns, controlled uniformity and reliability in the purity of the gases and the amount of hyperpolarization have become necessary. Also, the need for convenient and reliable generation of these hyperpolarized gases has become important for use in a clinical setting in which technicians, having little or no specific training in the laboratory techniques described above, are still able to provide discrete or continuous hyperpolarized noble gas samples to subjects undergoing MRI.

In view of the above considerations, it is clear that the apparatus and methods in use in the existing art are limited in a number of ways. For example, the existing art does not provide any practical means for refilling a spin exchange polarization chamber (cell) once it has been used. Most current chambers are either permanently sealed after the first filling or have been refilled with at best unsatisfactory results. Thus, it would be of benefit to develop means for effectively refilling a pumping chamber, or even for optically pumping in a continuous flow mode in the same chamber, so as to decrease costs of materials and personnel.

Moreover, even successful fills for the permanently sealed cells used previously were accomplished via a significantly different system. In the past, an expensive ultra-high vacuum system, with either oil-free pumps or cryotrapped oil-containing pumps, has been required in order to produce a sufficiently clean apparatus for filling high quality polarization chambers. Such a system is expensive (about $30,000), not very compact (3 ft by 6 ft footprint), and requires high maintenance by a trained vacuum technician. A new system, requiring only minimal maintenance and capable of being operated without specialized knowledge of vacuum technology, would be desirable. Also, a system having a more convenient size would be useful in clinical settings.

In addition, there has been no practical way to produce hyperpolarized gas in a continuous fashion. For each spin exchange hyperpolarization procedure a new sealed sample has had to be prepared and introduced into the hyperpolarization apparatus. It would, therefore, be desirable to develop a system which overcomes this limitation to provide means for continuous hyperpolarization of flowing noble gas.

Systems for producing hyperpolarized gases have also been quite bulky, typically requiring separate rooms for their installation. Such systems are not transportable. Thus, small, convenient hyperpolarizers would be advantageous. Also transportable systems would be of benefit in situations where space is a critical consideration.

Also, there has previously been no convenient way to store substantial quantities of hyperpolarized noble gases for later distribution in discrete quantities of arbitrary amount (up to liters of gas at atmospheric pressure). It would be important to overcome this limitation as well, to provide apparatus for continuous accumulation of a hyperpolarized noble gas, as well as storage and controlled release of the hyperpolarized gas on an as-needed basis, while still retaining substantial quantities of hyperpolarization.

SUMMARY OF THE INVENTION

Accordingly, as a result of the invention, there is now provided an improved apparatus and method for producing hyperpolarized noble gases. In particular, there is provided self-contained apparatus for producing and delivering large quantities of high purity hyperpolarized noble gases for use in magnetic resonance imaging.

In one embodiment, the apparatus includes a high capacity hyperpolarizer, in which a flowing noble gas, preferably xenon-129 or helium-3, can be hyperpolarized in substantially larger quantities than has been possible in the past. This hyperpolarizer includes means for hyperpolarizing a flowing noble gas in a continuous or batch mode. For example, the noble gas may be flowed through the hyperpolarizer's polarization chamber in a continuous mode, such that the rate of flow permits a substantial fraction of the nuclei to be hyperpolarized during their passage through the polarization chamber. This continuous flow approach is particularly well adapted to a noble gas having a relatively short polarization time, such as $^{129}$Xe. Alternatively, in a semi-continuous approach, the flow of the noble gas may be isolated or temporarily interrupted to enable hyperpolarization of the noble gas in discrete volumes. In this semi-continuous mode, a quantity or volume of the noble gas is hyperpolarized in the polarization chamber and thereafter the flow is resumed to deliver a discrete quantity or pulse of a noble gas. Also, subsequent volumes of the flowing gas can then be treated to provide episodic or periodic pulses of hyperpolarized gas. Helium-3 has a relatively long polarization time, i.e., up to several hours, and is preferably polarized using this episodic flow approach.

In this apparatus, the polarization chamber permits flow-through of the noble gas, either on a continuous or semi-continuous basis. Hence, the generation of relatively large quantities of the hyperpolarized noble gas is not impeded or otherwise limited by the need to prepare new hyperpolarization cells for each and every polarization.

In another embodiment, the hyperpolarizer apparatus of the invention further includes means for accumulating hyperpolarized $^{129}$Xe in a continuous or semi-continuous mode. This system enables hyperpolarized xenon to be flowed from the polarization chamber through a cryotrapping reservoir and trapped efficiently and selectively as frozen xenon. The accumulator permits xenon flowing within the reservoir to deposit on top of previously deposited xenon, thereby permitting the accumulation of the xenon ice. Because the solid form of hyperpolarized $^{129}$Xe has a much longer polarization lifetime than the gaseous form, the accumulator can serve as a storage device, allowing the accumulation of significant quantities of hyperpolarized gas for use at a later time.

The invention further includes a method of hyperpolarizing a noble gas in which a gas mixture of $^{129}$Xe is hyperpolarized. The gas mixture includes a minor quantity of xenon, a minor quantity of a fluorescence-quenching gas such as nitrogen or hydrogen, and a major quantity of a buffer gas. It has now been observed that the hyperpolarization of high partial pressures of xenon is not as efficient as desired, i.e., high pressure xenon can inhibit its own hyperpolarization by depolarizing the alkali metal too efficiently. Low pressure hyperpolarization therefore, has been the requisite norm. A new method of improving the efficiency of xenon hyperpolarization according to the invention, however, includes using a buffer gas to broaden the absorption of laser energy, thereby enhancing the efficiency of the hyperpolarization process. One preferred buffer gas is helium, although hydrogen can also be used. Accordingly, the invention includes the use of a buffer gas different from the quenching gas, to solve the problem that certain quenching gases cause depolarization of the alkali-metal vapor at high pressures of the quenching gas. Accordingly, a preferred gas mixture includes a minor mount of $^{129}$Xe, a minor amount of a fluorescence quenching gas, and the balance helium. More preferably, the mixture includes from about 0.1% to about 5% $^{129}$Xe, from about 0.1% to about 30% of a quenching gas such as nitrogen or hydrogen, and the balance helium. Most preferably, the mixture includes about 1% $^{129}$Xe, about 1% nitrogen, with the balance being helium. Alternatively, the mixture can include from about 0.1% to about 5% $^{129}$Xe, with the balance being hydrogen, wherein hydrogen performs quenching and pressure-broadening functions.

Accordingly, the invention provides a method for hyperpolarizing a flowing noble gas. The method includes:

a) flowing a target gas, which includes a noble gas, through a pumping chamber; and b) hyperpolarizing the flowing noble gas in the pumping chamber by spin exchange with alkali metal atoms;

thereby providing a flowing hyperpolarized noble gas.

The method preferably involves flowing the target gas through the pumping chamber at a rate which provides an average atom residence time of the noble gas of from about 0.5 to about 5 times the spin exchange time $\tau_{SE}$ between atoms of the alkali metal and the noble gas. More preferably, the flow rate provides an average atom residence time of the noble gas of from about 1 to about 3 times the spin exchange time $\tau_{SE}$ between atoms of the alkali metal and the noble gas.

The method can be performed such that the target gas is continuously flowed through the pumping chamber during the hyperpolarizing. This mode is preferred for noble gases such as $^{129}$Xe, having relatively short polarization times. Alternatively, the method can include temporarily disrupting (reducing or halting) the flow to isolate a discrete quantity of the target gas in the pumping chamber to permit hyperpolarizing of a quantity of noble gas. Flow of the gas is restored or increased once the desired quantity of the noble gas has been hyperpolarized to the desired degree. Noble gases, such as $^3$He, having longer polarization times are preferably polarized using this mode. In an episodic or periodic approach, this method is preferably performed at least twice, to provide two or more discrete quantities of the hyperpolarized noble gas to provide semi-continuous flowing delivery.

The method of the invention involves hyperpolarizing the noble gas by spin exchange with alkali metal atoms. A preferred alkali metal is rubidium, preferably including rubidium-85 and/or rubidium-87. Rubidium atoms have been found to be suitable for polarizing both $^{129}$Xe and $^3$He. In other applications, however, cesium (preferred for $^{129}$Xe) or potassium (preferred for $^3$He) may be desirable. Other alkali metals may be employed as needed.

The noble gas preferably includes a polarizable amount of a noble gas isotope having nuclear spin. Preferred noble gases include xenon, including $^{129}$Xe, and helium, including $^3$He. Other noble gases may be employed as required. Preferably, the isotope having non-zero spin is present in the noble gas in at least natural isotopic abundance. Enriched noble gases, i.e., having substantially greater proportions of the desired isotope than are found in nature are more preferred. Helium3, in particular, has a natural abundance in helium which is so low (i.e., $10^{-6}$) as to make enrichment necessary. Useful amounts of $^3$He (e.g., at least about 10%, preferably more than about 50% $^3$He) can be obtained by harvesting the $^3$He produced by the radioactive decay of tritium, and helium gas containing up to 100% $^3$He is commercially available.

In a preferred scenario, the target gas includes not only the noble gas, but further includes a quenching gas, which acts to suppress fluorescence by the alkali metal atoms during hyperpolarizing. Preferred quenching gases include nitrogen gas ($N_2$) and hydrogen gas ($H_2$).

A particularly preferred method involves using a target gas in which the noble gas includes $^{129}$Xe. In this case, the target gas includes a quenching gas, as well as a buffer gas which causes pressure broadening of the optical absorption spectrum at which the alkali metal atoms absorb suitable hyperpolarizing radiation. A highly preferred buffer gas is helium, which is substantially $^4$He. Hence, a useful target gas according to this embodiment includes a minor amount of $^{129}$Xe, a minor amount of nitrogen or hydrogen as the quenching gas, and a major amount of helium. More preferably, the target gas includes from about 0.1% to about 5% $^{129}$Xe, from about 0.1% to about 30% of the quenching gas, with the balance being helium. Still more preferably, the target gas includes about 1% $^{129}$Xe, about 1% nitrogen, with the balance being helium. Thus, the invention includes three-part target gases, in which the quenching gas and the buffer gas are different. However, target gases can include hydrogen as both a quenching gas and a buffer gas, e.g., about 0.1% to about 5% $^{129}$Xe, with the balance hydrogen.

In another embodiment, the hyperpolarization method further includes accumulating the hyperpolarized noble gas flowing from the pumping chamber. In the case of $^3$He, a large amount of $^3$He can be accumulated (at or above atmospheric pressure) in a gas storage reservoir. In the case of $^{129}$Xe, preferred accumulating means includes a cryotrapping reservoir which permits flow-through of gas, with the accumulation of $^{129}$Xe in frozen form, while limiting the accumulation of other gases, such as quenching and buffer gases initially present in the target gas mixture.

The method advantageously includes flowing the noble gas under hyperbaric or supra-atmospheric conditions. Preferably, the gas is flowed at a pressure of from about 1 atmospheres (atm) to about 30 atm. A presently preferred pressure is about 10 atm.

In a particularly advantageous approach, the noble gas (or target gas) flowed through the pumping chamber is substantially free of impurities which can interfere with the hyperpolarizing process. Thus, impurities such as alkali-metal-reactive impurities and impurities which would otherwise cause the alkali metal to deposit in solid phase in the pumping chamber should be removed. Also, particularly in the case of $^3$He, impurities which can depolarize the noble gas should be removed. Preferably, the purifying means removes (e.g., getters) impurities such as water vapor and oxygen introduced during gas manufacture or mixing prior to the hyperpolarizing procedure.

The hyperpolarizing method of the invention is enhanced by heating the pumping chamber and its contents during hyperpolarizing to increase the efficiency of the process. In addition, the various aspects and parameters of the process are desirably monitored and controlled by central control means, typically including a computer.

In a preferred embodiment, the invention also provides a method of hyperpolarizing $^{129}$Xe in a target gas. The target gas includes $^{129}$Xe, as well as a quenching gas for quenching fluorescence of alkali metal atoms during hyperpolarizing, and a buffer gas for pressure-broadening the optical absorption band of the alkali metal atoms, and the hyperpolarizing is performed under conditions sufficient to induce hyperpolarization of the $^{129}$Xe by spin exchange with alkali metal atoms, thereby providing hyperpolarized $^{129}$Xe. The buffer gas and the quenching gas are preferably different. Preferably, the quenching gas is nitrogen or hydrogen. The buffer gas is preferably helium or hydrogen. More preferably, the target gas includes from about 0.1% to about 5% $^{129}$Xe, from about 0.1% to about 30% of the quenching gas, with the balance being helium. Still more preferably, the target gas includes about 1% $^{129}$Xe, about 1% nitrogen, with the balance being helium.

In another embodiment, the invention includes apparatus for hyperpolarizing a flowing noble gas. In this embodiment, the apparatus includes:

a) a target gas delivery system adapted to deliver a flowing noble gas;

b) a pumping chamber for hyperpolarizing the flowing noble gas by spin exchange with alkali metal atoms; and c) hyperpolarization means for hyperpolarizing the flowing noble gas in the pumping chamber.

The target gas delivery system in this embodiment preferably includes a gas container capable of maintaining the noble gas under compression prior to flowing the gas through the pumping chamber. A high pressure gas canister or bottle or other such device may be employed for this purpose. Moreover, the delivery system should be able to deliver the target gas under hyperbaric conditions. The remaining parts of the target gas delivery system are preferably sealed to maintain the gas under hyperbaric conditions of from about 1 atm to about 30 atm, more preferably about 10 atm. Indeed, all of the parts of the apparatus of the invention which contact the gas, including the pumping chamber associated conduits and valves, should be operable using hyperbaric gas pressures, preferably from about 1 atm to about 30 atm. The target gas delivery system also preferably includes means for removing impurities, such as alkali-metal-reactive impurities and depolarizing impurities, from the flowing target gas prior to flow of the gas through the pumping chamber.

The pumping chamber in the apparatus is preferably adapted to admit hyperpolarizing radiation, i.e., radiation of a wavelength and energy sufficient to permit polarization of the noble gas by spin exchange with alkali metal atoms. Thus, at least one irradiation window is included in the pumping chamber. In situations in which irradiation is employed from more than one position or direction, additional irradiation ports can be included.

The apparatus also can include a receiving reservoir adapted to receive hyperpolarized noble gas flowing from the pumping chamber. For $^{129}$Xe, a highly preferred receiving reservoir includes a cryotrapping accumulator for accumulating $^{129}$Xe in a frozen state.

In a preferred embodiment, the apparatus is adapted to permit continuous flow of the target gas through the pumping chamber during hyperpolarizing. Alternatively, the apparatus should permit controllable isolation of a discrete quantity of the flowing noble gas in the pumping chamber during hyperpolarizing. For example, the apparatus may be valved to permit control of the flow rate so as the reduce or halt the flow temporarily, while permitting resumption or increase of the flow when desired.

The apparatus should be adapted to deliver the target gas through the pumping chamber at a rate sufficient to provide an average atom residence time of the noble gas in the pumping chamber of from about 0.5 to about 5 times, more preferably from about 1 to about 3 times, the spin exchange time $\tau_{SE}$ between atoms of the alkali metal and the noble gas.

The hyperpolarizing means in the apparatus of the invention preferably includes a laser system capable of delivering into the pumping chamber radiation sufficient for hyperpolarizing the noble gas via spin exchange with alkali metal atoms, such as atoms of rubidium, cesium, or potassium. While conventional types of lasers are compatible with the invention, it is preferred that the laser system employs at least one laser diode array. In a preferred apparatus according to the invention, the laser system includes two laser sources in opposing arrangement along a single optical axis, with the pumping chamber adapted to admit radiation from both lasers. Each of the two laser sources preferably includes at least one laser diode array. Two dimensional, or stacked, laser diode arrays are preferred, and can deliver substantial output power into the pumping chamber. The laser system of any of these embodiments preferably includes radiation focusing means to collimate, and more preferably focus, radiation emitted from the laser system. Such focusing means preferably includes a Fresnel lens.

The pumping chamber itself should admit hyperpolarizing radiation from the laser source(s). Preferred structures of the chamber include conical or truncated conical (frustoconical) structures, although in certain configurations a cylindrical cell is suitable. Preferably, the chamber is designed in conjunction with the laser system to maximize light delivery into the chamber and throughout its interior, to maximize the efficiency of the hyperpolarizing procedure.

Other apparatus is advantageously incorporated with the laser and pumping chamber. For example, the apparatus preferably also includes heating means for heating the pumping chamber during the hyperpolarizing procedure. Also, the apparatus desirably includes means for monitoring hyperpolarization in the pumping chamber, such as by NMR polarimetry. In addition, the pumping chamber preferably includes a fluorescence observation window, as well as fluorescence monitoring means for monitoring fluorescence through the fluorescence observation window.

Moreover, in continuously flowing systems, the apparatus preferably includes an alkali-metal vaporizer to provide sufficient alkali-metal vapor density in a flowing target gas to maintain good efficiency of the hyperpolarization process. In addition, the pumping chamber is desirably equipped with alkali-metal refluxing means to recover alkali metal vapor which might ordinarily leave the chamber with the flowing gas following hyperpolarizing. The vaporizer and the refluxing means can operate together to provide a continuous recirculation of the alkali-metal vapor through the pumping chamber. In preferred cases, the apparatus includes an amount of an alkali metal to permit maintenance of sufficient alkali-metal vapor density during a hyperpolarization procedure.

In another embodiment, the invention provides apparatus for hyperpolarizing a noble gas, most preferably $^{3}$He, which apparatus includes:

a) hyperpolarization means, including:

1) a laser system capable of delivering hyperpolarizing radiation, and 2) a computer system enabling control and monitoring of a hyperpolarization procedure; and b) a replaceable polarization unit, including:

1) a target gas delivery system for maintaining and delivering a target gas including a noble gas, preferably $^{3}$He, at a hyperbaric pressure, and 2) a pumping chamber in fluid communication with the target gas delivery system.

In this embodiment, the replaceable polarization unit is configured such that the unit is capable of engaging with and operating in conjunction with the hyperpolarization means so that the pumping chamber is oriented to transmit light energy from the laser source into the pumping chamber for hyperpolarization of the noble gas. Preferably, the apparatus is adapted to enable hyperpolarization by means of spin exchange between atoms of the noble gas and an alkali metal.

One desirable feature of the apparatus which involves a replaceable polarization unit is that a quantity of the target gas can be flowed into the pumping chamber, the quantity of noble gas can be hyperpolarized, and then the polarization unit can be removed from the hyperpolarization means to permit flowing delivery of the quantity of gas as desired, e.g., to a patient undergoing MRI. Immediately, another replaceable unit can be installed into the hyperpolarization means, to begin the flowing hyperpolarization of another quantity of gas. This mode of operation is particularly desirable with $^3$He, which requires relatively long polarization times.

In a further embodiment, the invention provides apparatus for use in hyperpolarizing a flowing noble gas, most preferably $^3$He, including:

a removable polarization unit, including:

a pumping chamber adapted to permit flow-through of a noble gas, and permissive to hyperpolarizing radiation for hyperpolarizing a flowing noble gas.

The polarization unit in this embodiment is adapted to removably engage and operate with a hyperpolarizing system including a laser system capable of delivering hyperpolarizing radiation into the pumping chamber when the polarization unit is engaged therewith. Apparatus according to this embodiment preferably enables spin exchange hyperpolarization of the noble gas.

This embodiment of the invention further provides apparatus, in which the removable polarization unit further includes a target gas delivery system, for maintaining and flowing through the pumping chamber a target gas including a noble gas to be hyperpolarized. The target gas delivery system preferably includes such a target gas, which includes the noble gas to be hyperpolarized.

Also in this embodiment, the pumping chamber can further include an amount of an alkali metal sufficient to maintain an alkali-metal vapor during a hyperpolarization procedure.

Other features of the apparatus of the invention described elsewhere herein can be incorporated into this embodiment. For example, the apparatus can include a removable polarization unit which further includes a heating system for heating the pumping chamber. Also, the target gas delivery system can further includes a target gas purifier for removing alkali metal-reactive impurities from the target gas prior to flow of the target gas through the pumping chamber. Alkali metal vaporizer means and refluxing means can also be included.

The polarization unit, including the elements of the target gas delivery system and the polarization chamber are preferably operable under conditions in which the target gas is under hyperbaric pressure, e.g., from about 1 atm to about 30 atm.

The invention also provides, in a further embodiment, apparatus for hyperpolarizing a flowing noble gas, preferably $^3$He, including:

a hyperpolarizing system, including:

a laser system for delivering hyperpolarizing radiation sufficient to enable hyperpolarization of a flowing noble gas.

In this embodiment, the hyperpolarizing system is adapted to removably engage and operate with a removable polarization unit having a multi-use pumping chamber adapted to permit flow-through of a noble gas, and to permit delivery of hyperpolarizing radiation into the pumping chamber when the polarization unit is engaged therewith. The hyperpolarizing system preferably enables spin exchange polarization of the noble gas.

The hyperpolarizing system preferably further includes a hyperpolarization monitoring system, e.g., an NMR polarimetry system, for monitoring the status of a hyperpolarization procedure. Moreover, the system can include a heating system for heating a pumping chamber of the removable polarization unit when such a unit is engaged therewith.

This type of hyperpolarizing system can further include an reservoir means for accumulating a flowing hyperpolarized noble gas. In this case, the accumulator is adapted to permit fluid communication with the pumping chamber when the removable polarization unit is engaged therewith. The reservoir means preferably permits flow-through of a target gas. In the preferred case involving $^3$He, the reservoir permits hyperbaric accumulation of the hyperpolarized $^3$He. Alternatively, hyperpolarized $^{129}$Xe can be accumulated in frozen form via selective cryotrapping of the hyperpolarized $^{129}$Xe gas.

In this embodiment, also, the laser system includes at least one, and preferably two, laser sources. When two laser sources are provided, they are preferably positioned in opposed arrangement along a single optical axis, such that hyperpolarizing radiation can be delivered from opposing directions into the pumping chamber when the polarization unit is engaged with the hyperpolarizing system. Whether one or more laser sources is employed, each laser source is preferred to include at least one laser diode array. As with other apparatus according to the invention, when two or more laser diode arrays are used, they are preferably held is a stacked arrangement.

These and other advantages of the present invention will be appreciated from the detailed description and examples which are set forth herein. The detailed description and examples enhance the understanding of the invention, but are not intended to limit the scope of the invention.

BRIEF DESCRIPTION OF THE DRAWINGS

Preferred embodiments of the invention have been chosen for purposes of illustration and description, but are not intended in any way to restrict the scope of the invention. The preferred embodiments of certain aspects of the invention are shown in the accompanying drawings, wherein:

FIG. 5 is an illustration of a transportable hyperpolarizer system according to the invention; and FIG. 6 is a schematic diagram of a removable polarization unit according to the invention.

DETAILED DESCRIPTION OF THE PREFERRED EMBODIMENTS

Figure 1:
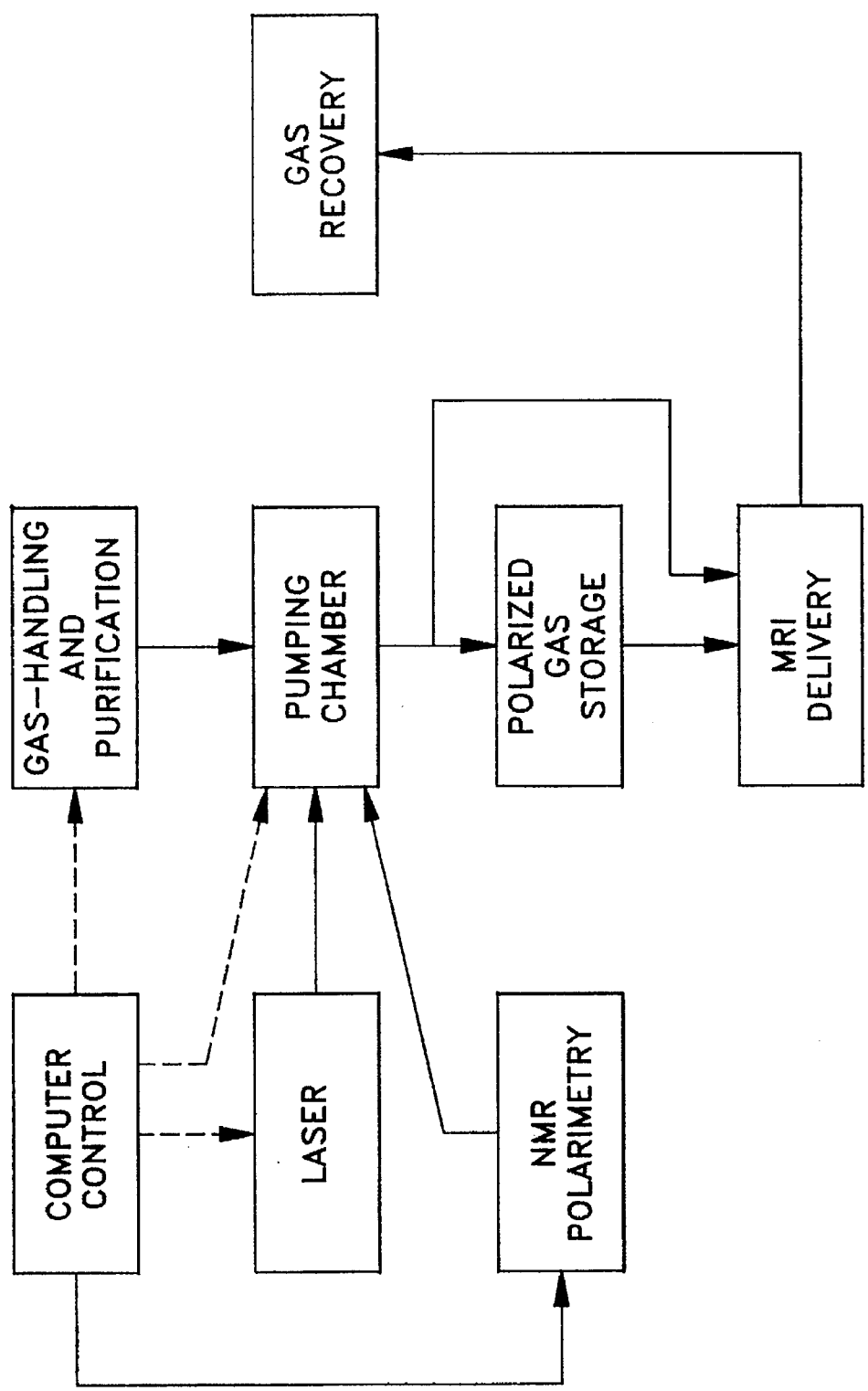
FIG. 1 is a block diagram illustrating the general configuration of a hyperpolarizer unit according to the invention.

In general terms, FIG. 1 shows a schematic block diagram of an integrated hyperpolarizer system useful for generating and accumulating large quantities of a flowing hyperpolarized noble gas according to the invention. In FIG. 1, a hyperpolarizer unit is shown which includes several major subsystems, including an MRI gas delivery subsystem through which the flowing polarized gas can be delivered as needed for imaging studies.

The pumping chamber shown in the diagram is the chamber in which the alkali metal optical pumping and alkali-noble gas spin exchange take place. Initially, unpolarized gas enters from the high purity gas handling subsystem and exits to the polarized gas storage chamber which accumulates the hyperpolarized gas.

The gas handling subsystem provides the proper supply of gases to the polarization chamber while generating and/or maintaining the gas purity required for the hyperpolarization process.

After having been polarized in the polarization chamber, the hyperpolarized gas may be flowed into the polarized gas storage chamber where it is accumulated and stored until use. The polarization chamber and the polarized gas storage chamber generally must be carefully prepared so as to maintain the gas polarization and may also function to separate the hyperpolarized noble gas from an inert buffer gas. When needed, the hyperpolarized gas will be flowed from this chamber to the MRI delivery subsystem.

The MRI delivery subsystem shown in FIG. 1 encompasses all the equipment required for respirating a subject on the hyperpolarized gas either from the polarized gas storage chamber or directly from the polarization chamber. This may include devices and systems to perform a variety of desirable functions, preferably including pressure regulation, virus filtration (HEPA, etc.), gas mixing to include oxygen, an appropriate MR-compatible breathing mask, etc. Typically, exhaled air is collected by the same mask and directed to the gas recovery subsystem. After being used for a subject, the gas is collected by the gas recovery subsystem so that it can be recycled for future use. The collected gas can be periodically shipped back to a central reprocessing location for purification and/or sterilization.

The polarimetry subsystem shown in FIG. 1 monitors the level of polarization of the gas in the polarization chamber or the gas storage chamber.

Also as shown in FIG. 1, the laser subsystem supplies the necessary photons (hyperpolarizing radiation) for the optical pumping process. The output beam of this system is directed into the polarization chamber.

The control subsystem is a unified computer-software and hardwired subsystem which controls and monitors the different processes occurring in the various subsystems.

Figure 2:
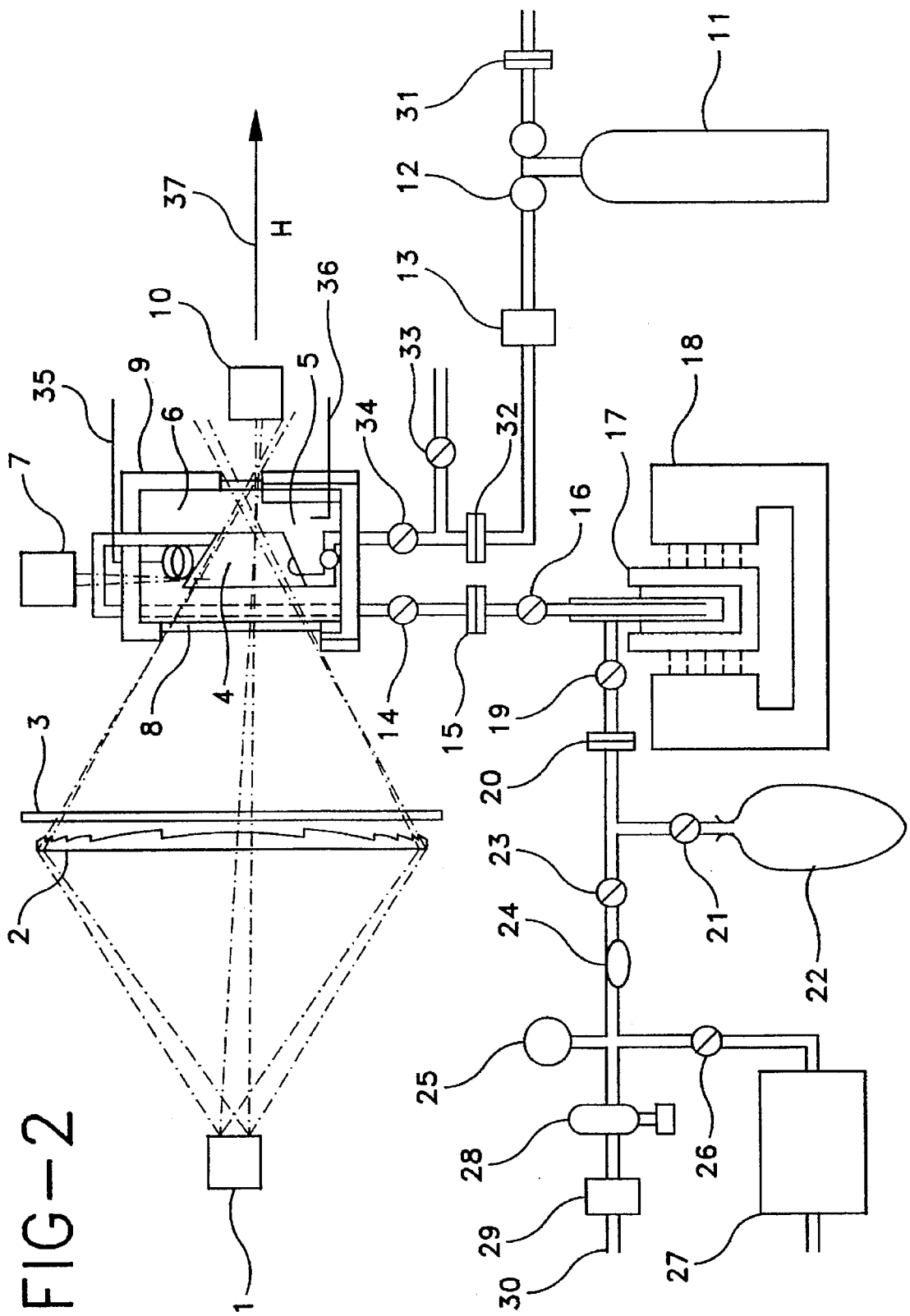
FIG. 2 is a schematic diagram illustrating a flowing hyperpolarizer and accumulator apparatus according to the invention.

FIG. 2 illustrates in somewhat greater detail an integrated hyperpolarizer system useful for generating and accumulating large quantities of a flowing hyperpolarized noble gas according to the invention.

In FIG. 2, a laser diode array 1, has an output power of from about 100 W to about 500 W and emits radiation of wavelength $\lambda$ suitable for absorption by alkali metal atoms. The wavelength spread $\Delta\lambda$ is about 2 nm FWHM, with a linear polarization of about 95% or greater. Because of the large spread in wavelength, this type of laser is referred to herein as a "broad-band" laser. In an alternative embodiment, two lasers pumping from opposite sides of the pumping cell 4 can be used, with appropriate redesign of the cell 4 and the optical diagnostics system 10.

An aspheric Fresnel lens 2 (typically plastic) directs most of the light from the diode laser array 1 into the optical pumping cell 4. An image of the diode face is formed just beyond the end of the optical pumping cell 4. Although the Fresnel lens is inexpensive and well adapted to currently available diode laser arrays, different optics may be more appropriate for future lasers which may have higher intrinsic brightness than those available today.

Quarter wave plate 3 converts linearly polarized light from the diode laser array to circularly polarized light. As shown, a plastic quarter wave plate is positioned just past the Fresnel lens 2 where the laser beam has expanded so much that heating of the lens and the wave plate is not a problem. The light from the laser 1, which is already linearly polarized to a high degree, can be passed through a linear polarizer (not shown) before it reaches the quarter wave plate 3 if the natural linear polarization is not sufficient.

Optical pumping cell 4 is shown, provided with saturated alkali-metal vapor, e.g., Rb or Cs, and an optimum gas mixture of $^{129}Xe$, $N_2$ and He, as described below in connection with the premixed gas tank 11. The cell 4 has the shape of a truncated cone to accommodate the converging light from the lens 2. Refluxed alkali metal from the exit pipe 6 drops back through the cell and collects in the vaporizer 5. The cell and associated piping must withstand the high pressure of premixed gas, typically from above about 1 atmosphere to about 30 atmospheres. High gas pressure inside the cell is important to permit efficient absorption of the broad-band light from a diode laser.

A vaporizer 5 is provided, in this case, upstream of the pumping cell 4 for loading the flowing gas mixture with alkali-metal vapor prior to the gas's entry into the cell. The vaporizer 5 can be made of crumpled wires of copper or other non-magnetic metal or sintered metal that is readily wetted by liquid alkali metals (e.g., a metallic sponge). The vaporizer 5 is soaked with liquid alkali metal, and stuffed into a receptacle of appropriate materials and dimensions to ensure full loading of the gas with vapor. The flow velocity of the gas, the distance through which it flows, and the pore diameter of the "sponge" are adjusted to ensure that the gas is fully saturated with alkali-metal vapor before it enters the optical pumping cell. The vaporizer eliminates problems of small surface area of the alkali-metal droplets in the optical pumping cell, which often causes the gas to be undersaturated with vapor in the optical pumping cell.

It should be noted that other means can be used for loading the noble gas with alkali-metal vapor. For example, a mixing chamber can be employed having means for providing alkali-metal vapor to a relatively static quantity of gas prior to infusion into the polarization chamber. Such an approach would be advantageous in systems and methods in which the flow is modulated or interrupted.

The vaporizer 5 illustrated in FIG. 2 is replenished by gravity flow of condensed alkali metal from a refluxing outlet pipe 6, which leaves the cell in a substantially vertical orientation. The refluxing outlet pipe 6 causes the alkali-metal vapor in the gas exiting the cell to condense on the walls of the pipe. The dimensions and flow velocity are adjusted to ensure that most of the alkali metal condenses and drips back into the optical pumping cell by gravity flow, eventually returning to the vaporizer. Thus, the vaporizer and reflux condenser together act as a recirculating alkali-metal supply system for flowing hyperpolarizers according to the invention.

A fluorescence monitoring detector 7, e.g., including a charge-coupled-device (CCD) camera and appropriate filters, is provided to observe the weak, unquenched $D_2$ fluorescence from the optically pumped alkali-metal vapor. The fluorescence monitoring arrangement can be adjusted for use with two lasers pumping from either side of the cell.

Insulating window 8 is provided to permit pumping light to enter the oven 9 and the optical pumping cell 4. This window and other light-transmitting surfaces may be provided with an antireflection coating. Similar windows are provided for the fluorescence monitor 7 and the optical multichannel analyzer (OMA) 10.

Oven 9 is provided to keep the optical pumping cell at a temperature appropriate for absorbing most of the useful light from the diode laser. Typical operating temperatures for rubidium are from about 100° C. to about 200° C. Somewhat lower temperatures are appropriate for cesium which is more easily volatilized. The oven can be heated by flowing hot air or by internal, non-magnetic electrical heaters. Optical multichannel analyzer (OMA) 10 for measuring the efficiency of absorption of light from the broad-band diode laser array. A different arrangement of the OMA is required if the cell is pumped from both sides. OMA systems suitable for use in the apparatus of the invention are commercially available.

A high-pressure tank 11 is included to maintain a premixed target gas at a pressure of several hundred atmospheres. Preferred target gas constituents, by partial pressure, are:

a. from about 0.1% to about 5% $^{129}$Xe (or xenon of at least about natural isotopic composition) for hyperpolarization in the optical pumping cell 4 and accumulation in the xenon accumulator 17;

b. from about 1% to about 3% $N_2$ for quenching fluorescence in the optical pumping cell 4. $H_2$ may be used at somewhat higher partial pressures (e.g., from about 1% to about 30%) in place of $N_2$ to take advantage of the smaller spin depolarization cross-sections of alkali-metal atoms in $H_2$ gas compared to $N_2$ gas;

c. the balance of the gas is a buffer gas, preferably He, for pressure broadening the optical absorption lines of the alkali-metal atoms in the optical pumping cell 4. The He gas pressure is adjusted to ensure that it causes negligible spin depolarization compared to the xenon. Other gas mixtures may be employed impart quenching and pressure-broadening qualities to the target gas.

A pressure regulator 12 is employed to reduce the very high pressure of the premixed gas in the storage tank 11 to a pressure appropriate for the optical pumping cell 4. This is typically from about 10 to about 30 atmospheres, depending on how much pressure broadening is needed for optimum use of the broad-band laser light.

Gas purifier (getter) 13 is used to remove trace impurities, mainly water vapor, from the premixed target gas stream.

As shown in FIG. 2, the accumulation reservoir 17 for accumulating xenon includes a counterflow cold trap—cooled by liquid nitrogen or some other cryogen in a Dewar vessel. Closed-cycle refrigerators can also be used for cooling. Such systems would not be included in apparatus dedicated to $^3$He.

Detachment point 15, together with the detachment point 20, permits the removal of the accumulation reservoir 17. Valve 14 isolates the optical pumping cell 4 from the detachment point 15, and controls flow therebetween. Valve 16 is used to isolate the accumulation reservoir 17 from detachment point 15.

A permanent magnet 18 is provided to produce a static field of greater than about 500 Gauss (0.05 T) at the location of the frozen xenon in the accumulator reservoir. A field this large is adequate to obtain the longest possible spin-lattice relaxation times (e.g., about 3 hours at liquid nitrogen temperatures). For lower condensation temperatures, where much longer spin-lattice relaxation times are attainable, larger magnetic fields are needed. The magnet may also be contained inside the cryogenic assembly and kept cool along with xenon accumulation reservoir.

Valve 19 is employed to isolate the xenon condenser 17 from the detachment point 20, which together with detachment point 15 permits removal of the xenon condenser 17.

Valve 21 is used to release sublimed hyperpolarized $^{129}$Xe gas to transfer bag 22 or to any other container for transport of hyperpolarized $^{129}$Xe gas at atmospheric pressure for various uses, e.g., MRI of patients, non-destructive evaluation, etc. Hard-walled containers can be used to transport the hyperpolarized $^{129}$Xe gas at other pressures.

Valve 23 isolates the xenon accumulator 17 during sublimation of the condensed xenon and gas transfer to the bag or other receptacle 22.

Glass-to-metal seal 24 is provided, with the piping on the pump side of the seal preferably being stainless steel or other metal. On the xenon-condenser side of the seal, the piping is glass. Similar glass-to-metal seals on the input side of the gas flow and appropriate stress-relieving bellows are not shown, but are normally to be preferred.

Pressure gauge 25 is used to monitor and control pressure during the accumulation phase.

Pump 27, isolated by valve 26, is used for evacuating any remaining He and $N_2$ from the xenon condenser 17 at the end of the accumulation period.

A needle valve 28 or other flow control device is included to permit waste He and $N_2$ gas to vent to the room or to a recovery container for reuse. This valve 28 controls the flow rate through the optical pumping cell 4. The venting rate is adjusted to optimize the preparation of hyperpolarized $^{129}$Xe according to principles we have developed. Flow of the gas is monitored by flow meter 29.

A vent 30 is provided, leading to the atmosphere or to a collection receptacle for spent buffer gas (e.g., He) and quenching gas (e.g., $N_2$ or $H_2$).

Port 31 is included for purging the gas lines with clean gas (e.g. argon, helium or nitrogen) through the vent 24 after the tank of premixed gas is attached. Vent 33 permits release of the purging gas introduced at the port 31.

Attachment point 32 is supplied for connecting the premixed gas supply to the optical pumping cell. Valve 34 isolates the optical pumping cell during purging of the gas-supply piping.

A nuclear magnetic resonance pickup coil 35 is also included to monitor $^{129}$Xe polarization in the pumping chamber, which is useful for optimizing the gas flow rate.

Temperature sensor 36, e.g., a resistive temperature device (RTD), is employed to monitor the temperature of the oven.

A static magnetic field 37 is also illustrated. The source is not shown, but we have successfully used either Helmholtz coils or the fringing fields of a magnetic resonance imaging magnet or a combination of the two.

A control subsystem (not shown) is generally desirable as a unified computer-software and hardwired subsystem which is used to control and monitor the different processes occurring in the various subsystems.

Figure 3:
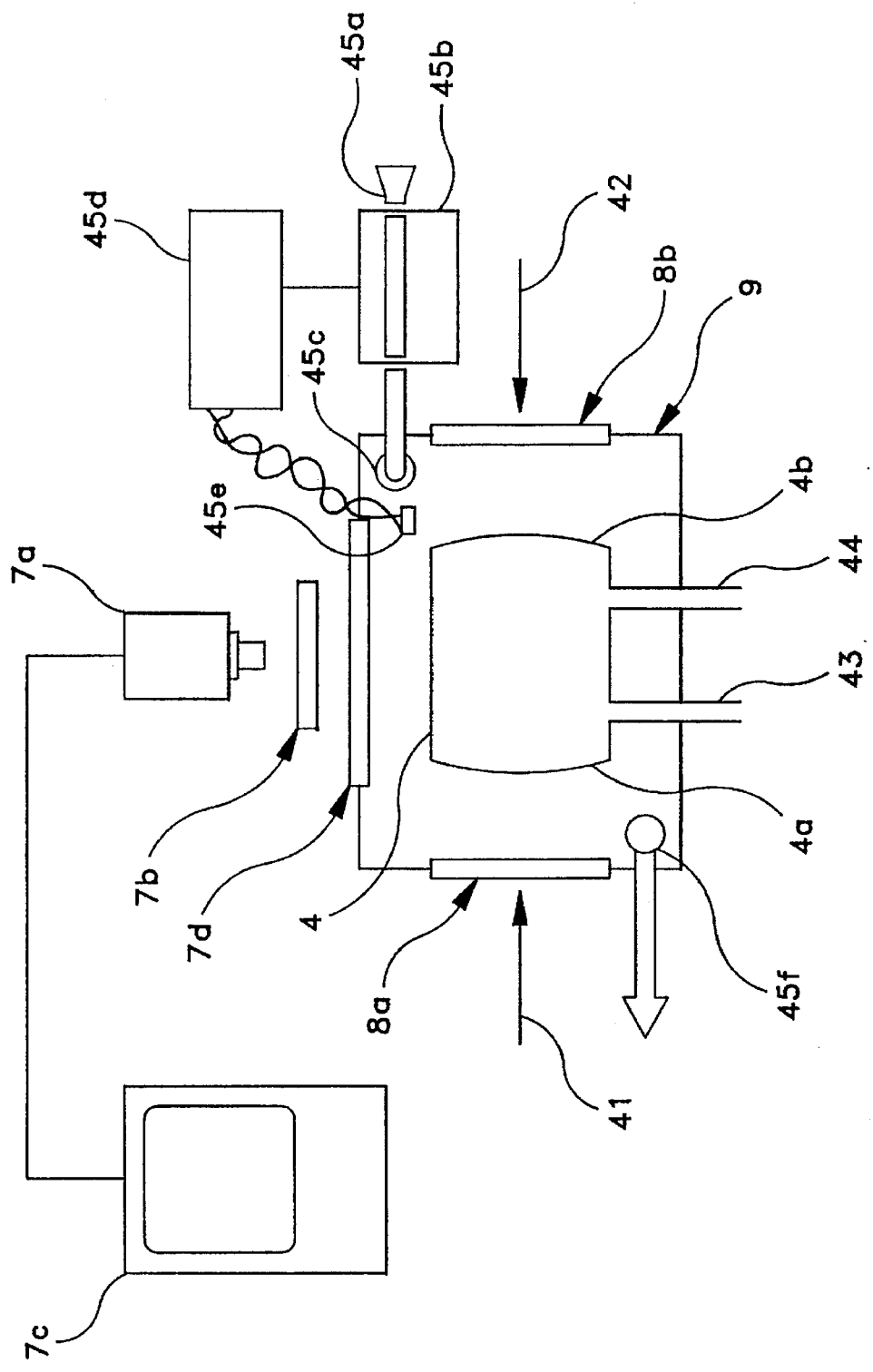
FIG. 3 is a schematic diagram of a continuous or episodic flow polarization cell according to the invention, including certain associated apparatus.

FIG. 3 illustrates one configuration of a hyperpolarization system according to the invention, including additional details concerning certain components of the polarization chamber. The drawing shows a polarization chamber (cell) 4, an oven 9 in which the cell 4 is housed, and heating and control apparatus 40a–f necessary to maintain the oven 4 at a chosen temperature.

One implementation of a polarization chamber is shown in FIG. 3. As the chamber in which the optical pumping and spin exchange takes place it must satisfy a number of requirements. For example, the pumping chamber must hold an appropriate amount of polarizable gas in a substantially leak-tight environment. The gas pressure in the chamber is maintained according to the requirements of the apparatus, preferably being maintained at a pressure above atmospheric pressure (also designated herein "hyperbaric") up to about 30 atm, and more preferably from about 8 atm to about 12 atm for a glass cell. The gas pressure may be outside (above or below) this range, as required. A presently preferred pressure is about 10 atm, which reflects the structural limitations of glass, the material most typically used in the manufacture of polarization chambers. Higher pressure or gas density could be used in other polarization chamber structures.

The pumping chamber 4 shown in FIG. 3 is a preferred embodiment having two light ports or windows (4a and 4b) for admitting hyperpolarizing radiation (arrows 41 and 42) into the cell from two lasers (not shown) arranged to emit along the same axis but from opposite directions. Regardless of whether one or more than one light port is employed, the ports are preferably at least substantially transparent to light at and/or near the wavelength of the optical pumping transition line of the alkali metal being used (i.e., "hyperpolarizing radiation"). For example, the wavelength of the $D_1$ transition in rubidium is 794.7 nm, and the light ports suitable for use with rubidium should be at least substantially transparent to light at this wavelength. Other alkali metals are hyperpolarized using other wavelengths, and the light ports should be transparent to the appropriate wavelength. Optimization of pumping efficiency would require that the light ports be as transparent as possible to light of the requisite wavelength, i.e., absorption oft he hyperpolarizing radiation should be minimized. They may be antireflection-coated to maximize light transmission.

The volume-averaged relaxation time of the nuclear polarization of a gas in the pumping chamber must be sufficiently slow compared to the spin-exchange rate between the alkali-metal atom and the noble-gas nucleus to allow the desired level of polarization in the cell to be attained. The materials and design of the polarization chamber must therefore be selected with care. For example, the pumping chamber should be chemically compatible with alkali metals, preferably being compatible with alkali metals at temperatures appropriate for optical pumping (e.g., up to about 200° C. or more). In addition, if an NMR polarimetry system is used to monitor the hyperpolarization procedure, it is preferred that the pumping chamber walls not interfere substantially with the rf field required for polarimetry.

The particular implementation of the pumping chamber will depend on the type of gas being polarized. As noted above, polarization chambers useful according to the invention can be made of glass. The glass should be resistant to the alkali metal(s) employed in the spin exchange process. For $^3$He, moreover, the pumping chamber is preferably made from a glass having a limited permeability to helium. More preferably, the glass has a helium permeability which is smaller than that of Corning 7704 (Pyrex®). Such glasses are exemplified by aluminosilicate glasses (such as Corning 1720), or metal-sealing borosilicate glasses (such as Corning 7052 or Schott 8502). For $^{129}$Xe, on the other hand, there is no stringent need for limited permeability since xenon is a substantially larger atom, and permeability is not a significant problem. Another useful glass is glass which is prepared to be substantially free of iron. For lower temperature applications, standard borosilicate laboratory glassware, e.g., Pyrex®, Duran®, can be used.

The pumping chamber preferably has a conical or truncated conical (frustoconical) shape, to provide a gas volume which conforms substantially to a converging beam of hyperpolarizing radiation. By focusing (converging) the laser radiation into a cell with decreasing diameter along the optical axis, the light intensity at regions of the cell distal to the laser is effectively increased to at least partially offset the decrease in intensity which occurs due to absorption of the light in the proximal regions. Nonetheless, cylindrical pumping cells may be desirable in certain implementations. Hourglass-shaped cells (i.e., cells resembling two cones opposed at their apices) can be desirable to implement and maximize the efficiency of opposed laser systems.

Presently, the pumping cells are made of glass. Other pumping chamber designs, capable of higher pressure operation, can be employed. Cells with pressures in excess of 10 atmospheres can be readily made by using metal walls and piping with appropriate optical windows to admit the light. It is also possible to design glass optical pumping cells contained within a high-pressure surrounding gas or a transparent liquid (e.g., pump oil), in an external cell with appropriate windows. Then the pressure differential across the inner cell walls is minimized, and there is no danger of breakage.

Previously, sealed cells have retained the hyperpolarization gas in contact with the walls of the cell for extended periods, providing ample opportunity for the gas to relax by interacting with iron and other paramagnetic impurities. An advantage of the continuous or semi-continuous hyperpolarization system of the invention, however, is that the hyperpolarized noble gas need not be in contact with glass for any prolonged period. We have found that because of this feature, the need for removing paramagnetic impurities in the glass is reduced, permitting use of less expensive materials.

The pumping chamber 4 also desirably has separate reseatable inlet and outlet ports, such as o-ring valves, which allow continuous or episodic removal and replacement of the gas being polarized. Any suitable gas ports permitting flow control can be employed. The chamber 4 can have a single gas port through which gas is flowed into and out of the cell episodically. However, for flowing gas in a continuous fashion, two gas ports are required. Such an arrangement is shown in FIG. 3, in which inlet port 43 and outlet port 44 are shown. The remainder of the gas handling system is not shown in this drawing.

The reseatable gas ports include valve means for controlling the flow of gas. Typically, these valves have Pyrex® glass bodies and stems, and are fitted with flexible and elastic seals which are also resistant to alkali metals. Such seals are typically o-rings, and can be made of various polymeric materials. A preferred o-ring material, which has shown virtually no susceptibility to alkali attack, is a copolymer of ethylene and propylene. Other polymers which may be suitable include silicone polymers. Fluoroelastomers such as Viton™, Teflon®, etc., are relatively less resistant to alkali attack, and are therefore less desirable, albeit suitable for short term use. Resistance of the o-rings to alkali attack is an important characteristic since oxidation of the pumping chamber can occur should oxygen enter the chamber through failed o-rings.

The valves in the reseatable gas inlet and outlet apparatus are separated from the main body of the pumping chamber by conduits, preferably tubes made from glass similar to that used for the polarization chamber. See conduits 43 and 44 in FIG. 3. These tubes allow the heat sensitive o-ring materials to be thermally separated from the main body of the cell and the oven surrounding the cell, which, during the polarization process, is often heated to above the o-ring's limit. The tubes also help limit the net polarization relaxation due to interaction of the hyperpolarized noble gas with the valve body. This is believed to be related to the use of high operating gas pressures, at which pressures diffusion down the length of the tubes is slow compared to the depolarization time constant of the bulk volume (which is dependent upon the ratio of tube volume to total volume). Also, capillary tubes limit the degree to which the hyperpolarized gas, particularly $^3$He, can contact (diffuse into) and be depolarized by the valve seals. Valves constructed of non-ferrous metals could also be used.

We have found that the pumping cell will have a longer $^3$He polarization lifetime if the stock glass tubing is entirely reblown during the fabrication of the cell. Reblowing means that every interior surface is made molten and reformed during fabrication. An acid rinse with a strong acid, such as $HNO_3$ or HCl, can also be used to improve polarization lifetime, but alone is not as effective as reblowing.

When the interior surfaces of the glass are sufficiently clean and the chamber is fabricated according to the procedures described herein, no significant relaxation of the noble gas polarization occurs relative to the time scale of the spin-exchange process. A detailed description of such procedures is found in Middleton, H. L., *The Spin Structure of the Neutron Determined Using a Polarized $^3$He Target*, Ph.D. Dissertation, Chapter 5, Princeton University, (1994). This description is incorporated herein by reference. Briefly, the interior cell walls are cleaned by baking them at up to 500° C., either while the cell is under vacuum or while it is being purged with a pure buffer gas. A radio frequency (rf) discharge may also be run inside the cells to assist in driving contaminants from the surface. After being cleaned, the cells are not exposed to the atmosphere but are either kept under vacuum or kept filled with the pure purge gas until the alkali-metal and the noble gas are introduced. Since the alkali metal is typically driven into the cells by heating a reservoir of the metal, all of the connecting gas/vacuum lines between the cell and the reservoir must be alkali metal-resistant and cleaned of volatile adsorbed species in a manner similar to the cell cleaning method. After the alkali metal is loaded into the cell, the desired amount of the target gas is introduced and the cell is sealed off, at which point it is ready to be polarized.

Other improvements in reduction of gas depolarization can be advantageously incorporated into the apparatus of the invention. For example, metal-film coatings (gold, alkali-metals, etc.) may improve polarization lifetimes and reduce the effort required in cleaning and fabricating cells. We have found, for instance, that gold does not induce any significant relaxation of the nuclear polarization and can thus serve a good wall coating material. Polymeric coatings such as those described in U.S. patent application Ser. No. 08/478,276, filed Jun. 7, 1995, can also be employed beneficially.

Another method of improving the cleaning process includes employing a low pressure gas purge concurrent with an rf discharge.

A third alternative method includes fabricating the cells from machinable, non-ferrous metals to allow for high gas pressures. Such an interior surface may require coating with an appropriate metal or polymer film. Moreover, laser ports would then have to be added to allow the introduction of laser light into the cell. Since the radio frequency used for the NMR polarimetry is only tens of kHz, the skin depth of the metal may be such that the metal walls will not interfere with the NMR. Alternatively, the polarimetry can be omitted, performed in a separate storage chamber, or accomplished optically by measuring the frequency shift of the alkali EPR frequency due the presence of the polarized $^3$He.

A fourth approach would be to fit the cells with an alkali metal ampule having a mechanical seal that could be opened after the remainder of the cell is cleaned. For instance, a thin glass window could be broken by a small glass bead or by the noble gas pressure when the cell is filled. Such a system would reduce the amount of handling of alkali-metal required during the cell-filling process.

Still another advantageous technique includes manufacturing the storage chambers for previously polarized noble gas so as to be substantially identical to the polarization chamber, except that the requirements of alkali-metal chemical resistance and transparency to the optical-pumping laser light may be relaxed. This becomes of especial importance in the accumulator reservoirs useful according to the invention. We have unexpectedly found that, because the relaxation of the hyperpolarized $^{129}$Xe is so efficiently depressed in the frozen state, the quality of manufacture of the walls of the reservoir is of lesser importance. This feature, therefore, enables lower quality standards to be observed, with concomitant cost savings.

We find that alkali-metal vapor tends to be lost from a flowing gas polarization chamber during even modest gas flows (10–20 cm$^3$/min) if significant precautions are not taken. This has previously been a substantial impediment to the development of refillable or continuous flow cells. We have observed, for example, that the rubidium absorption resonance and $D_2$ resonance can completely disappear under unfavorable conditions. Our study indicates that the major source of rubidium loss in a flowing gas system is due to gettering of impurities (presumably $H_2O$ and $O_2$) by the rubidium vapor. Small amounts of these impurities in the supply gas would ordinarily have only a vanishingly small effect on the rubidium in a sealed cell. Flow of gas, however, appears to provide a continual fresh supply of such alkali-reactive impurities into the polarization chamber, resulting in continuing and substantial diminution of available alkali vapor. Our present understanding is based on our finding that this loss of rubidium vapor can be substantially prevented by installing an in-line gas purifier, such as one of the nitrogen purifiers (getters) available from Ultra-Pure Systems, Inc. Such purifiers have been found to clean the feed gas sufficiently so that rubidium vapor loss is virtually eliminated at a wide range of flow rates. Such purifiers are typically designed for the purification of nitrogen, but they also pass the noble gases without problem, and have been found to be ideally suited for purification of, for example, a He:Xe:$N_2$ mixture preferably employed according to the method of the invention.

Another, less significant, loss of rubidium occurs as the rubidium leaves the cell as gas is flowed through the cell. We have overcome this problem in several ways. First, rubidium loss can be limited by ensuring that the temperature of the conduit leading away from the pumping cell is low enough to secure the deposition of the rubidium on the conduit walls. Room temperature is normally adequate. No additional filter or trap is required, although a cold trap may be employed to ensure complete rubidium removal in medical applications. Second, and more preferably, refluxing apparatus can be used. For example, a refluxing outlet pipe may be used to condense the alkali-metal vapor. The dimensions of the pipe and the gas flow velocity can be adjusted to ensure that most of the alkali metal condenses and drips back into the pumping cell by gravity flow. Accordingly, an outlet conduit leaving the pumping chamber in a substantially vertical orientation will take advantage of such gravity flow this configuration is illustrated in FIG. 2. In non-flowing systems such as the sealed cells commonly used previously, such reflux is clearly unnecessary since the alkali metal cannot escape from such sealed cells.

Nonetheless, despite such precautions, the alkali metal in the pumping chamber will eventually become oxidized or used up. In that event, the pump chambers themselves can be easily recycled. Current procedure is to rinse the chamber with warm water, and then dry in an oven. The cell can the be recoated with a coating agent such as dimethyldichlorosilane and reattached to a manifold. The cell can then be baked out overnight, and a vacuum drawn. It is then ready for reinstallation on the hyperpolarizer. Cells can be recycled in this manner numerous times without detectable degradation in performance.

As mentioned briefly above, FIG. 3 also shows the oven 9 which houses the polarization chamber 4. The optical pumping oven operates in a temperature range which is limited by loss of alkali-metal vapor polarization at unduly high temperatures. Maximizing the temperature without sacrificing rubidium polarization maximizes the spin exchange rate, allowing for faster accumulation of polarized noble gas. Typically, the temperature range for the oven is from about 80° C. to about 200° C. A preferred temperature is in the range of from about 105° C. to about 150° C. For example, a temperature of about 150° C. provides a Rb-$^{129}$Xe spin exchange time of about 22 s, and an average rubidium polarization of about 50%. About 20–30% of the laser light is absorbed by the rubidium at this temperature. A temperature of about 130° C. may be preferred since the $^{129}$Xe NMR signal drops precipitously at higher temperatures. At 130° C., the Rb-$^{129}$Xe spin exchange time is about 65 s, roughly a factor of three lower than the time at 150° C. Accordingly, flow rates would have to be lower at lower temperatures, resulting in lower yields of polarized $^{129}$Xe. It has also been found that laser-induced heating causes a higher (~20° C. higher) effective cell temperature (and thus a higher rubidium number density ([Rb])) than is reflected by the oven thermometer.

By controlling gas flow rate and temperature in the polarization chamber, the degree of polarization and total volume of the hyperpolarized gas produced can be adjusted. For a given available laser power and bandwidth, the temperature of the pumping chamber will be set as high as possible without significant sacrifice to the volume-averaged polarization of the alkali-metal vapor. This optimization determines the spin-exchange rate $\gamma_{SE}$ at which polarization is transferred to the noble gas. The flow rate will preferably then be adjusted so that a noble gas atom spends on average about 1–3 spin exchange time constants ($1/\gamma_{SE}$) in the polarization chamber. A hotter chamber will result in faster spin exchange, thus allowing higher flow rates of the gas. Flow settings can be verified by comparing the noble gas NMR signal against the flow rate. If the flow is too fast, the noble gas signal will drop because the sample does not have a chance to fully polarize.

The oven should be constructed so as to minimize the creation of magnetic-field gradients capable of inducing nuclear relaxation in the noble gas. Preferably, the oven is constructed of materials that do not create gradients sufficient to induce significant nuclear relaxation in the noble gas. The oven materials should also retain substantial structural integrity at temperatures up to at least about 250° C. High temperature plastics or aluminum are suitable choices. Ferromagnetic materials such as steel generate magnetic field gradients which can rapidly depolarize the noble gas, and are therefore less desirable materials. A discussion of this effect may be found in the Middleton dissertation, referred to elsewhere herein.

As noted above in reference to FIG. 3, the illustrated oven 9 is provided with two or more laser windows 8a and 8b positioned to which permit laser light (arrows 41 and 42) to pass into and out of the oven along the optical axis of the system. (The optical axis is defined as the path, containing the laser, optics, and the cell, along which the laser light travels.) The oven is preferably oriented so that the optical axis is aligned with the direction of the applied magnetic field necessary for optical pumping. Preferably, the oven windows 8a and 8b do not significantly impair the transmission of the laser light through reflection and/or absorption. They may be antireflection-coated to maximize light transmission.

Again referring to FIG. 3, the oven may also be equipped with a fluorescence observation window 7d. Preferably, the observation window is oriented to permit visualization of the polarizing chamber from a position substantially perpendicular to the optical axis. This window 7d allows the observation of $D_2$ resonant fluorescence resulting from optical pumping of an alkali-metal vapor. FIG. 3 further illustrates fluorescence visualization means. Typically, such means includes a video camera 7a and monitor 7c, equipped with a $D_2$ filter 7b, for observing the fluorescence. The image can be used to tone the laser wavelength, to optimize the optical pumping temperature, as well as to align the laser.

The oven should be heated by means of materials and in a manner that satisfy the same conditions for minimizing magnetic-field gradients as described above. As shown in FIG. 3, in a preheated embodiment, compressed air in conduit 45a is passed over a filament heater 45b situated several feet away from the oven 9. (The heater is placed at a distance to minimize the field gradients created by the current running through it.) The hot air is then flowed through the oven 9 via inlet 45c to attain the desired temperature. A temperature controller 45d actuates the heater based on the reading of a temperature sensor 45e inside the oven. Hot air is vented through outlet 45f. The sensor 45e should be non-ferromagnetic to avoid the generation of field gradients. In an alternative approach, a high rf electrical heater may be used to heat the chamber. Use of such high frequency rf power is inherently devoid of the types of gradients which might interfere with the polarization.

In a preferred embodiment of the apparatus of the invention, the pumping chamber's valve assembly remains outside of the oven. This reduces both deterioration of temperature sensitive o-rings, and limits the migration of potentially harmful alkali metal toward the valve.

The gas handling and purification system can incorporate numerous features. The system introduces a controllable mixture of gases into the polarization chamber while simultaneously insuring sufficient purity in the gas stream to prevent significant degradation of the quality of the polarization chamber. The polarization-chamber quality is determined by the $T_1$ (polarization lifetime) of the hyperpolarized gas within it. It is known that the polarization chamber quality is affected both by gaseous impurities and by contaminants on the walls.

The polarization process requires both the polarizable noble gas (typically anywhere from 0.1 atm to tens of atm) and a small amount (generally 10 to 100 Torr) of a quenching gas (usually nitrogen, but perhaps hydrogen or others). The quenching gas improves the efficiency of the optical pumping process. For hyperpolarizing $^{129}$Xe, it is preferred to also include a large amount of a buffer gas (generally from about 1 atm to a few tens of atm), which acts to broaden the alkali-metal absorption line and to improve the polarization efficiency. See below for greater detail concerning the buffer gas.

One type of plumbing-design implementation for the target gas handling system includes separate pathways for introducing the low-pressure (nitrogen) and high-pressure gases. In this way a separate low-range pressure gauge may be isolated from the high-pressure gasses in order to prevent its rupture. It has been found that chemical or cryogenic getters should be placed in the gas flow lines as needed to increase the gas purity. Since varying purities of gas are available, the amount of additional purification will be established based on measurements of the polarization-chamber degradation vs. either number of times refilled (if discrete charges are used) or total operating time (if a continuous-flow system is used). Even high purity gases however, have been found to contain enough impurities, such as $O_2$ and $H_2O$, to cause significant degradation of the cells within a relatively short period of flow or after a few refills.

With a multiple-gas handling system, the filling of a cell proceeds as follows to get discrete charges of polarized gas. First, any residual inert buffer gas in the system is evacuated using the roughing pump. Second, the small amount of nitrogen required is introduced into the polarization chamber and the low-range pressure gauge valved off. Next, the gas to be polarized and any additional high-pressure buffer gases are introduced and the polarization chamber is valved off once the desired pressures are attained.

A continuous flow into the pumping chamber can be accomplished by inserting metering valves into the different gas flow lines and using a flow meter on the exhaust port of the polarization chamber to calibrate flow vs. pressure-gradient and metering valve setting. Since only a small amount of nitrogen is required, it may be difficult to set its flow rate given the much larger flow rates of the other gases. Since the nitrogen strongly affects the fluorescence coming from the polarization chamber during optical pumping, this can be overcome by calibrating the nitrogen flow rate vs. the total fluorescence coming from the chamber during optical pumping.

While the multiple-gas handling approach is workable, and has the advantage of permitting adjustment of the gas mixture on a continuing basis, it is more preferred to employ premixed gases. In a highly preferred embodiment, a pre-mixed gas is supplied directly to the polarization chamber from a single reservoir without need for adjusting relative flow rates. This simplifies the operation of the system, and renders the polarization process more reproducible and consistent. For example, the proportions of the gases in the mixture are invariant over time and between hyperpolarization procedures. Suitable gas mixtures are discussed elsewhere herein, and may be obtained from commercial sources.

It should be understood that because the hyperpolarizing apparatus of the invention permits hyperpolarization of a noble gas on a continuing basis, the gas delivery system is preferably configured to permit easily controlled and consistent gas mixtures to the pumping chamber. In larger scale systems, a single gas handling system can be used to supply the target gas, serially or simultaneously, to two or more polarizing systems. Separate control means can be provided to allow individual control of gas flow to each of the pumping cells.

In any case, all of the gas handling plumbing lines must have their interiors cleaned prior to filling a polarization chamber. This prevents contaminants from evolving off of the interior surfaces and being carded into the polarization chamber, where they could degrade its surface. This cleaning may be accomplished through moderate heating of the plumbing lines to about 100° C. while purging the lines with an appropriate, high-purity inert buffer gas and or evacuating the lines. If a combination of purging and evacuating is performed, these methods may be performed in simultaneous or sequential combination.

Once the gas is flowing into the polarization chamber and the hyperpolarizing is begun, the procedure should be monitored. In particular, the condition of the gas contents in the chamber should be determine as the hyperpolarization proceeds. NMR polarimetry is a preferred method for monitoring the gas polarization in the polarization chamber (cell). The system is preferably able to operate in applied magnetic fields of order 10 G, corresponding to NMR frequencies of tens of kHz for $^{129}Xe$. Generation of an NMR signal is accomplished by placing an inductive coil near the cell. The coil is part of a timed circuit which resonates near the NMR frequency. Because of the low frequencies involved, tuning can be done in a separate tuning box well away from the coil and connected to it through coaxial cable.

The polarimetry subsystem functions according to typical NMR principles. There are two stages in generating an NMR signal: radio-frequency (rf) excitation and signal acquisition. A single rf pulse is delivered to the coil at or near the Larmor frequency to excite a small fraction of the spins, which subsequently precess about the applied magnetic field. The precession is detected as it generates a small voltage in the same coil. The signal-voltage is amplified, heterodyned, filtered, and digitized for analysis and display on a computer. Other circuit components serve both to shut off important detection components during rf excitation (muting mixer) and to prevent leakage rf from reaching the coil during signal acquisition (isolation mixers and diode gate).

To effectively monitor the polarization, the size of the signal should be directly proportional to the polarization of the gas. This is accomplished without significant depolarization of the sample by using a small excitation (flip) angle in conjunction with a surface coil, which excites only a small fraction of the nuclei. Although the process of generating the signal effectively destroys polarization, the number of nuclei affected is negligible compared to the entire sample. Yet this small fraction of spins typically generates a sufficiently strong NMR signal if the gas is hyperpolarized. If the rf excitation is executed reproducibly, the signal generated in this small fraction of nuclei is proportional to the polarization of the entire sample. The system is calibrated to yield an absolute value of the polarization (0–100%) by comparing the polarized gas signals to those of a water sample having the same geometry, for which the thermal-equilibrium polarization can be calculated. The method of low-field pulsed-NMR to do polarimetry is a significant advance over the prior art of Adiabatic Fast Passage (AFP), particularly as it becomes more desirable to polarize larger and larger volumes, because AFP requires a strong rf excitation of the entire sample volume.

Alternatively, a separate outlet bulb can be fitted to the polarization chamber to permit accumulation of a test sample of the polarized gas. The bulb can be measured in an Adiabatic Fast Passage (AFP) apparatus, which can yield much better NMR signals than pulsed NMR on the pump chamber. This apparatus can be calibrated to provide an experimental measurement of the gas polarization, which can be used to further refine the adjustment of the accumulation parameters.

In a preferred embodiment, the entire hyperpolarization system can be run from a desktop computer equipped with a few special circuit boards. One such board generates the necessary radio frequency pulses through Direct Digital Synthesis (DDS). Another desirable circuit board is an analog-to-digital converter (ADC board), which digitizes the signal. The latter circuit board also generates the (TTL) gating pulses which switch the muting and isolation mixers.

The laser subsystem of the hyperpolarization apparatus supplies the photons (hyperpolarizing radiation) necessary to the optical pumping process. Preferably, the photons are supplied by one or more laser-diode arrays producing continuous wave (cw) power. However, any laser system that provides sufficient power at the alkali-metal $D_1$ or $D_2$ lines may be acceptable. High pressure operation such as that described herein, however, has been found to require lasers capable of delivering more than 10 W, and preferably more than 50 W of power. Conventional lasers capable of delivering such power are prohibitively expensive to purchase and operate. Moreover, such lasers are bulky and require expensive and more or less permanent installation. For transportable or integrated hyperpolarization units, such lasers are too unwieldy. In such embodiments, the laser-diode arrays become highly preferred because of their compactness and efficiency, as well as their relative cheapness to acquire and operate.

Figure 4:
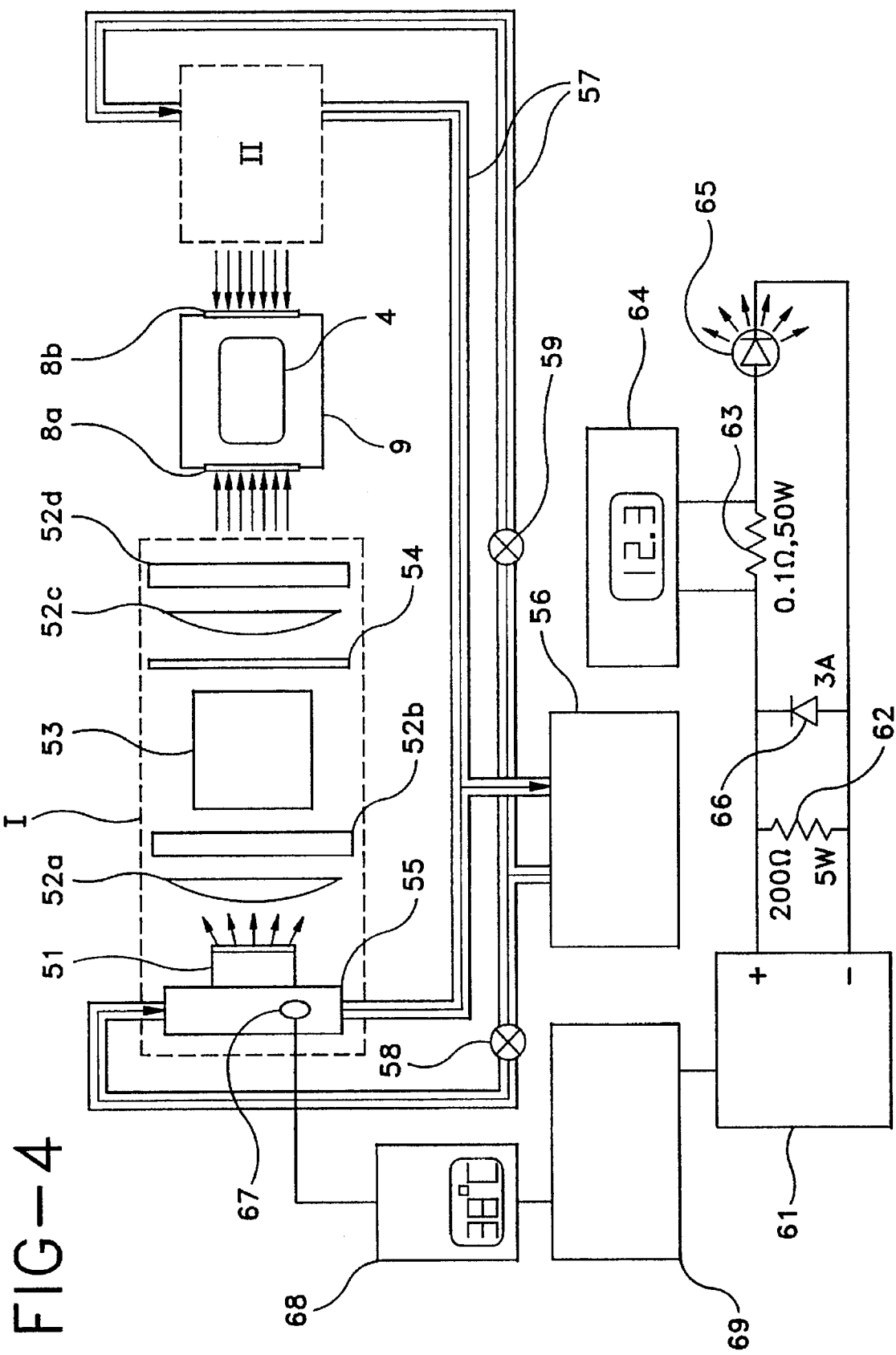
FIG. 4 is a schematic diagram of a hyperpolarizer unit of the invention, indicating the structures of single and dual laser systems according to the invention.

FIG. 4 is a schematic illustration of a laser subsystem suited for use in the apparatus of the invention. The top part of FIG. 4 shows an optical arrangement for the laser diode(s), while the bottom part of the figure shows the electrical configuration. The arrangement of optical elements, shown in the dashed box, represents one of several ways to prepare the emitted light. The light travels along the optical axis, substantially parallel to an applied magnetic field, through the oven windows and into the cell. The optics are adjusted to maximize the volume within the cell absorbing the light. As noted above, a converging or focused beam is preferred, together with a converging cell structure, to maximize the absorption of the hyperpolarizing radiation along the axis of the cell. Optionally, a second similar laser and set of optics directs light into the cell along the same optical axis, but from the opposite direction. The electrical configuration consists of a power supply and several circuit elements necessary for monitoring and protection of the laser diode(s).

Unlike conventional lasers which emit coherent light of a single wavelength (extremely narrow profile), diode array lasers are broad-band devices whose emissions have a spectral width. i.e., typically emitting light at a continuous band of wavelengths. Normally, this spectral width is relatively narrow, appearing as a broadening around some principal wavelength, and being only about 1–5 nm wide. Lower power GaAlAs diode arrays have been employed for spin exchange polarization of $^3$He. Chupp et al., *Phys. Rev. A* 40(8):4447–4454 (1989) describes the use of an approximately 1-W diode array, and Cummings et al., *Phys. Rev. A* 51(6)4842–4851 (1995) describes a 20-W diode array. For the method and apparatus of the present invention, the power of the diode arrays is preferably significantly larger, being above about 50 W, and more preferably above about 100 W.

The choice of laser emission wavelength λ is determined by the choice of the alkali metal used for spin exchange. As noted, the laser should emit at about the $D_1$ (or $D_2$) transition line of the desired alkali metal. For rubidium, λ is preferred to be about 795 nm, while for cesium, λ is preferred be about 894 nm. Thus, for rubidium, the laser can be a GaAlAs laser. The use of cesium rather than rubidium metal, however, permits the use of more reliable, aluminum-free diode laser arrays (e.g., InGaAsP lasers), lower operating temperatures, and 13% more photons per watt because of the longer resonance wavelength for Cs. A currently preferred laser diode array (available from Opto Power, of Tucson, Ariz.) is a GaAlAs laser diode array, comprising 10 bar diodes in a stacked arrangement, which develops about 125 W of continuous wave (cw) power, can be tuned to a peak wavelength of 794.44 nm, and exhibits about 2 nm full spectral width at half maximum (FWHM).

Should lasers with narrower bandwidths become competitive (efficiency, cost, etc.) with conventional arrays in the future, less line-broadening buffer gas would be needed than for the presently available lasers mentioned above. This would permit use of higher proportions of xenon in the target gas mixture, which in turn would improve the yield of the accumulator apparatus. Lower pressure operation would also simplify some engineering problems with respect to the hyperpolarizer.

Also unlike conventional lasers, diode laser emissions are typically highly divergent, requiring optical correction to concentrate the light at a desired focus. The optical elements illustrated in FIG. 4 include, inter alia, a laser diode array 51, one or more (cylindrical or aspheric) lenses 52a–52d, a polarizing beam-splitter cube 53, and a quarter-wave plate 54. The lenses 52a–52d collimate and/or focus the laser light through window 8a to a beam size generally conforming to the dimensions of the polarizing cell 4 within oven 9. Depending upon application, the optics at least substantially reduce the divergence of the beam, rendering the beam collimated or more preferably providing a converging beam. We have found that circularly polarized converging light with angles as large as 30° from the magnetic field direction can efficiently spin-polarize alkali-metal atoms. The lenses are divided into two sets: one set each for independent horizontal (52a and 52c) and vertical (52b and 52d) movement and focusing of the light. FIG. 4 also illustrates indirectly a preferred, optional, laser system in which a second laser is employed to direct hyperpolarizing radiation into the cell 4 via window 8b in oven 9. The optional second laser system is identified as the dashed box II at the right side of the drawing, and should include substantially the same elements included within the dashed box I at the left side of the drawing.

We have unexpectedly found that simple aspheric Fresnel lenses can be used to focus the light from the diode arrays. These inexpensive lenses do converge transmitted light, but do not normally provide focus sufficient to generate a crisp image. This lack of focus, however, is not a significant limitation, and the use of such lenses helps reduce the cost of the hyperpolarizer over other types of installations which employ substantially more expensive cylindrical lenses. Other light collection arrangements are also possible, for example, microlenses on the diode array, or combinations of mirrors and lenses.

The beam-splitter cube 53 divides the incoming light into its two separate orthogonal linear polarizations. One polarization is reflected at 90 degrees to the optical axis and absorbed by a beam-block (not shown). The other polarization passes through to the quarter-wave plate 54, which converts the linearly polarized light to the circularly polarized light necessary for optical pumping.

As shown in FIG. 4, the laser-diode arrays 51 are each mounted to a brass cooling block 55, through which water flows to and from a heat exchanger 56 via cooling fluid conduits 57, and valves 58 and 59. The heat exchanger 56 may be anything from a recycling chiller with a secondary water circuit to a simple radiator, depending on laser power. Also as shown in FIG. 4, in a multi-laser setup, a single heat-exchanger unit can be used to supply both lasers, with valves or separate heater units on each set of water lines to control the temperature of each laser independently. Alternatively, each laser may be provided with its own heat-exchanger.

The laser-diode array is electrically driven by the circuit also diagramed in FIG. 4, or by another circuit equivalent thereto. The precise rating of the power supply 61 depends on the number of laser diodes and whether they are arranged in series or in parallel. For a single laser, for example, the power supply can be a DC supply rated at about 20–40 V, and about 20–40 A. Again referring to FIG. 4, the 200-ohm shunt resistor 62 reduces the intensity of any voltage spikes coming from the supply 61. The 0.1 ohm series resistor 63 and the DC voltmeter 64 are used to monitor the current through the laser diode 65. The parallel reverse-biased Schottky diode 66 protects against an inadvertent wrong-polarity connection of the laser diode 65. The current is adjusted and the current limit is set using the controls on the power supply 61. A thermocouple 67 mounted directly to the cooling block 55 monitors its temperature in the event that this temperature exceeds a set point, a high-limit temperature detector 68 trips a manual-reset relay switch 69 and shuts down the power supply.

One feature of spin exchange hyperpolarization of helium is that it can be performed at relatively high gas pressures, something which is not possible with metastability exchange methods. This provides an advantage over metastability exchange inasmuch as it is inherently less work to decompress a gas than to compress it. As noted hereinabove, complex apparatus is necessary to compress $^3$He produced by metastability exchange by up to two orders of magnitude to obtain usable pressures (~1 atm) of the gas.

Previously, it has been recognized that hyperpolarized $^3$He can be produced at high polarizations by means of spin exchange at high pressures (~10 atm). We have found however, that this is not possible when using high pressures of $^{129}$Xe. Specifically, the efficiency with which xenon depolarizes rubidium vapor is surprisingly high. We estimate that, neglecting molecular contributions, 0.1 atm of xenon has about the same spin destructive effect as 270 atm of helium. As a result, it is now believed that xenon pressures in excess of about 1 atm will result in very low rubidium polarizations for all but the most intense (i.e., thousands of watts) pump lasers.

For example, for a diode laser, a laser intensity of about 20 W/cm$^2$ (or 100 W/5 cm$^2$) would result in a Rb electronic polarization of only about 25% at the front of a chamber containing 10 atm of xenon. This polarization level only decreases toward the back of the chamber so that only small polarization volumes can be tolerated, with correspondingly small yields of polarized $^{129}$Xe.

The use of lower pressures of xenon can result in higher Rb polarizations, but at a substantial penalty. Low gas pressures give narrow Rb D$_1$ resonance lines and thus allow only a tiny fraction of the broad spectral output of the diode array (2 nm FWHM) to be used. Furthermore, the spectral hole burning that results from a narrow D$_1$ resonance again means that only very small volumes of Rb can be polarized, yielding small quantities of polarized $^{129}$Xe. For example, a 20 cm$^3$ cell containing 0.5 atm of xenon, and having a wall relaxation of time of 1000 s will at optimum give a $^{129}$Xe polarization of 56%, while using only 2.3 W of 100 W incident on the cell. The resulting 10 cm$^3$ of polarized gas (at 1 atm) is not sufficient for most applications of interest.

In typical hyperpolarization procedures, unpolarized $^{129}$Xe is placed in a sealed pumping cell along with a few tens of Torr of a gas (often nitrogen) which quenches the fluorescence of laser-excited rubidium atoms, thereby aiding the optical pumping process. We have unexpectedly found, however, that a buffer gas can be added to the sample to broaden the alkali metal resonance line, allowing for more efficient absorption of the broad spectral output of current high-power laser diode arrays. Without this high-pressure buffer gas, very little (about 1%) of the light from the diode laser can be absorbed because of the broad spectral bandwidth of the diode laser array (2 nm or more) and the very narrow (0.01 nm) absorption bandwidth of alkali metal atoms at low pressure. To achieve this effect, the buffer gas should not induce significant spin destruction of either the alkali-metal vapor or the $^{129}$Xe during optical pumping. A highly preferred buffer gas is helium, naturally having an isotopic abundance of 99+% $^4$He, but other gases having similar properties may be employed.

We have observed that increased buffer gas pressures induce the absorption band of rubidium to broaden, and that gas pressures of order 10 atm or more are preferred to achieve the desired broadening. Due to xenon's inherent capacity to destroy alkali-metal polarization, however, it is believed that samples containing 10 atm or more of pure xenon would not be usable. By contrast, it has been found that helium is quite non-destructive to the polarized alkali-metal spins and can be used as a line-broadening agent without penalty. Hydrogen can serve both as a quenching gas and a buffer gas to broaden the optical absorption line. Nitrogen is not as good a gas for this purpose as hydrogen or helium, because it causes substantial spin depolarization of the alkali metal atoms.

Accordingly, preferred gas mixtures for hyperpolarization of $^{129}$Xe according to the method of the invention would include a substantial proportion of the buffer gas, e.g., helium, with a minor but significant amount of $^{129}$Xe. For example, the mixture can include from about 0.1% to about 5% of xenon containing at least a natural isotopic abundance of $^{129}$Xe, from about 0.1% to about 3% of N$_2$, with the balance being helium. Most preferably, the mixture includes about 1% of $^{129}$Xe, about 1% of N$_2$, and about 98% helium. Alternatively, if the quenching gas is hydrogen, from about 1% to about 30% of the gas mixture should be hydrogen, with a corresponding reduction in the net proportion of helium. For helium, the gas mixture is simpler, since no benefit is gained from including a buffer gas. As for $^{129}$Xe, however, helium gas mixtures preferably include an amount of nitrogen or hydrogen as a quenching gas comparable to the amount used for $^{129}$Xe.

The low partial pressures of Xe used in the preferred method give rise to several problems. First, polarized $^{129}$Xe must be separated from the helium to attain useful concentrations of $^{129}$Xe. Second, the polarized $^{129}$Xe must be pressurized so that it can be extracted from the polarization apparatus. Third, while high $^{129}$Xe polarizations are attained on very short timescales, the yield of polarized gas from the pump chamber is very small. We have now found that freezing the polarized $^{129}$Xe into a solid (T<160K) solves all three of these problems.

To produce laser-polarized $^{129}$Xe in significant quantities, we have taken advantage of the extremely long spin-lattice-relaxation times T$_1$ of solid $^{129}$Xe. It has been demonstrated that once polarized, $^{129}$Xe can be frozen into a solid with little loss of polarization. As detailed in Gatzke et al., *Phys. Rev. Lett.*, 70(5):690–693 (1993), relaxation times are much longer in the solid phase than those which have been achieved thus far in the gaseous phase.

It is now possible, by means of cryotrap accumulator apparatus, to take advantage of the properties of xenon ice. Specifically, it is now recognized that the three-hour relaxation time of $^{129}$Xe in ice at liquid nitrogen temperatures permits the pumping and continuous accumulation of polarized $^{129}$Xe for up to three hours at a time. The use of even lower temperatures can extend the potential accumulation period further.

Once the flowing target gas is hyperpolarized, the entire gas stream ($^{129}$Xe, helium, and nitrogen) can be flowed through an accumulator. Details of an especially preferred accumulator for $^{129}$Xe are described in copending patent application Ser. No. 08/622,865, entitled "Cryogenic Accumulator for Spin-Polarized Xenon-129", filed on even date herewith, the entire disclosure of which is incorporated herein by reference. The accumulator includes a cryostat, preferably operating in the temperature range of from about 4.2 K. to about 157 K. A temperature of about 77 K. is preferred due its convenience, i.e., about the temperature of liquid nitrogen (b.p.=77 K.) which is a readily available refrigerant. However, lower temperatures are generally preferred, since longer polarization lifetimes can be obtained as the temperature of accumulation and storage are decreased.

In any event, polarized $^{129}$Xe passing through the cryostat immediately freezes due to its melting point being 157K. At low enough temperatures, the nitrogen may also freeze, but this should have no deleterious effect on the $^{129}$Xe polarization and long $T_1$. Hydrogen may be substituted as the quenching gas to avoid this problem. The bulk of the gas, i.e., the helium, simply passes through the cryostat and out through the exit port. Hence, a useful feature of this method is that it can be used to effectively separate the hyperpolarized xenon from the other, unwanted, components of the target gas mixture.

Because the relaxation time $T_1$ of frozen $^{129}$Xe is significantly longer when maintained in an applied magnetic field, the cryostatic accumulator is preferably fitted with a small permanent magnet capable of such magnetic-field strengths in order to improve holding times. The primary consideration in choosing the strength of the applied field is that the field should enable accumulation and/or storage for a period of about the maximum possible spin-lattice relaxation time at the accumulation/storage temperature. Accordingly, the applied field should be at least about 500 G (0.05 T) at liquid nitrogen temperatures. We observe, however, that the selection of field strength is dependent upon the temperature at which the $^{129}$Xe is being accumulated or stored. Specifically, lower temperature accumulation and/or storage benefits from the use of higher field strength.

The apparatus described herein is capable of integration with MRI imaging systems consistent with the systems described in U.S. Pat. No. 5,545,396. Typical of such systems is a commercially available MR imaging unit including a 2-Tesla, 30-cm horizontal Omega CSI magnet (G.E. NMR Instruments, Fremont, Calif.) and associated apparatus, described in greater detail in Middleton et al., *Magn. Reson. in Med* 33:271–275 (1995). The ability to produce large quantities of hyperpolarized noble gas can now be employed beneficially to permit the accumulation and storage of sufficient gas prior to imaging that no additional hyperpolarizing need be undertaken during the imaging itself. Thus, one or more subjects can now be imaged in a clinical setting using a single source of previously accumulated xenon. Alternatively, imaging can now be undertaken in which a continuous hyperpolarization procedure generates a continuing source of hyperpolarized gas supplied to a subject for study of respiration or other physiological processes enabled by the extraordinary properties of the noble gases. Previously, imaging of this sort was either impossible or extremely impractical due to the small amounts of hyperpolarized gases available for use.

In one preferred embodiment, the hyperpolarizer apparatus of the invention is a freestanding integrated unit, which is substantially self-contained and convenient to use. For example, the apparatus can be configured into a movable cart system with a footprint of about 2 feet by 6 feet. In this embodiment, the unit includes the laser system, a gas source, a polarizing cell, NMR polarimetry systems, power supplies, and a computer which is programmed to control and monitor most or all of the systems.

The laser subsystem of the hyperpolarizer system unit preferably includes one or more high power diode laser arrays, a power supply for the lasers, protection circuitry, a cooling unit and assorted optics for controlling and directing the laser energy.

The control subsystem includes a computer system, such as a personal microcomputer or workstation, components for monitoring the polarization by NMR as the procedure is performed, and components for monitoring and maintaining the cell temperature during the procedure. For example, the rf for the polarimetry can be provided using direct digital synthesis, as described elsewhere herein.

Ideally, the hyperpolarizer system also includes a number of safety systems, including interlocks, limit switches, non-computer controlled relays, etc.

Preferably, the integrated polarization system includes a replaceable polarization cartridge unit, which includes all of the components with which the gas has contact during the polarization procedure. Thus, the polarization unit can include a high pressure gas bottle containing enough gas to provide a substantial hyperbaric flow of gas during the hyperpolarization. The polarization unit further includes the pumping cell. Inlet and outlet conduits, respectively leading to and from the pumping cell, are included. These include valves for controlling the flow of gas into and out of the cell. For convenience, the polarization cartridge can also include some or all elements of the pumping oven, as well as the polarimetry probes. Other elements such as pressure transducers, regulators, and gas purifiers can also be included as desired.

The polarization unit is designed to permit easy its straightforward insertion into and removal from the hyperpolarizer system unit. The cartridge should be of a size and weight so as to promote ease of handling and installation. Applicants believe that a suitable polarization unit can be approximately 30 cm by 50 cm by 10 cm or roughly equivalent thereto. At this size the essential components can be included without unduly impairing handling of the unit. One structure capable of satisfying these various design requirements is described in detail below.

Another convenient feature of the replaceable polarization unit is that the target gas is preferably supplied premixed in a single bottle. This permits formulation and use consistent target gas mixtures, and avoids the necessity of having the operator of the unit control the gas mixture, thereby simplifying operation of the unit. Nonetheless, the polarization unit can, alternatively, include separate bottles for each gas to be mixed into the target gas.

FIG. 5 illustrates one embodiment of a transportable hyperpolarizer system unit according to the invention. In this embodiment, two laser diode arrays 100a and 100b are mounted on the top of a wheeled cart 101. Optics subsystems 102a and 102b are provided to collimate the laser energy, directing the energy to a focus at the pumping cell 103. The pumping cell can be mounted separately or as part of a replaceable polarization unit subsystem, described below. In FIG. 5, the pumping cell 103 is shown as part of such a polarization unit 110. Accordingly, the hyperpolarizer may be viewed as a docking station into which the polarization cartridge can be inserted to engage and operate with the systems on the hyperpolarizer. The hyperpolarizer system further includes a power subsystem including a power supply 120, a main power safety 121 and other protection circuitry 122, each having controls and displays as necessary. A cooler system 125 is provided to modulate the operating temperature of the lasers. A shelf 127 provides an emplacement for a microcomputer (not shown) for controlling and monitoring the polarization process. The cart 101 further includes a cover 105 to confine the laser light. Similar systems may be permanently or semi-permanently installed in, for example, a wall mount or a fixed electrical rack system. Other configurations are within the scope of the invention. Preferably, each of the main systems and subsystems are easily replaceable, such as being integrated into the unit via plug and jack connections.

FIG. 6 provides a schematic illustration of one embodiment of a replaceable polarization unit according to the invention. A gas bottle 201 is provided which contains the target gas including a noble gas such as $^3$He or $^{129}$Xe. Suitable gas mixtures, as described herein, are available from gas suppliers, such as Isotec, Inc. Miamisburg, Ohio. The gas bottle is capable of maintaining the target gas under high pressure, and includes enough gas to permit several high pressure fills of a pumping chamber 221 or which permits high pressure continuous flow through the chamber sufficient to produce the requisite amount of hyperpolarized noble gas. An important advantage of the polarization unit is that it can be replaced easily when the gas supply is exhausted. Moreover, replacement polarization units can be manufactured and shipped fully configured for installation into a hyperpolarizer system, and can be stored indefinitely in reserve.

The gas bottle 201 is in fluid communication with a pressure regulator 203 via conduits 205 and 206, controlled by valve 207. The pressure regulator 203 controls the gas flow, and is preferably a high purity regulator such as a stainless steel two stage ultra-high purity (UHP) regulator (e.g., Model E99-OLRC available from Air Products). Valve 207 and other valves in the cartridge which contact the gas should be operable under high pressure. Suitable valves include all metal Nupro valves Model SS-4BG-VCR available from Penn. Valve & Fitting Co., Willow Grove, Pa.

Conduit 209 leads from the regulator 203 to a flow-through pressure transducer 211, and flow is controlled by valve 213. Valve 213 is used to regulate flow when filling the cell with a new gas charge. Cell pressure is monitored by the flow-through pressure transducer 211. The transducer 211 is preferably bakeable to about 200° C. Suitable transducers include, for example, Model HS-10S available from Hastings NALL Mass Flowmeters or Model 212FT available from Setra Systems, Inc., Acton Mass.

Transducer 211 is in fluid communication with gas purifier 215 via conduit 217. The purifier 215 is desirable for removing water vapor and other impurities from the target gas, since such impurities can interfere with the polarization process. The purifier 215 is preferably a getter device, such as the mini purifier vessel available from Ultra-Pure Systems, Inc., Colorado Springs, Colo. Typically, such devices are heated to improve purification, e.g., by an external band heater with a thermocouple (e.g. available from Ultra-Pure Systems, Inc.)

Conduits 219 and 220 connect the purifier 215 to the pumping cell 221, and is controlled by valve 223. The pumping cell 221 is manufactured as described elsewhere herein and has a volume of about 10 cm$^3$ to about 100 cm$^3$, preferably about 30 cm$^3$. Pumping cell 221 also includes an outlet vent 225, which is controlled by a valve 227.

Conduit 219 branches to provide conduit 220 to the pumping cell and conduit 229 to valve 231. Then conduit 233 leads from valve 231 and branches to provide conduit 235 leading to diaphragm pump 237 (controlled by valve 239) and conduit 241 leading to a purge outlet 243 and controlled by valve 245.

This gas delivery configuration permits convenient purging of the system, which is important to maintaining the efficiency of the hyperpolarization procedure. A purging protocol can proceed as follows: First, a hot clean purge gas is injected into the purge inlet 247, traveling through conduit 249, controlled by valve 251. Next, the purge gas passes through the regulator 203, the pressure transducer 211, and the purifier 215. By opening valves 231 and 245, the purge gas can be vented through the purge outlet 243. In principle, valves 223 and 227 can be used to purge the cell, however, it is believed that this will not be necessary as a routine matter. Finally, the diaphragm pump 237 can be used to remove residual purge gas through valve 239 following the purge.

The following examples are provided to assist in a further understanding of the invention. The particular materials and conditions employed are intended to be further illustrative of the invention and are not limiting upon the reasonable scope thereof. In particular, certain considerations applicable to polarization of noble gases according to the invention are exemplified herein with reference to polarization of flowing $^{129}$Xe by spin exchange with rubidium atoms. However, this description should not be understood as limiting the scope of the invention. Such considerations apply in the polarization of $^3$He, such as in a semi-continuous flowing mode, as well as in the use of other alkali metals, such as cesium and potassium. Exceptions and variations to these generalizations, such as they are known, are noted herein where relevant, without taking away from the general applicability of the invention.

EXAMPLE 1

A continuous flow polarization apparatus according to the invention has been constructed generally in accord with the structure illustrated in FIG. 2, described above.. The pumping chamber is a glass cylinder 6 cm long and having a volume of about 30 cm$^3$. The optical axis is collinear with the longitudinal axis of the chamber.

We have found that the optimal flow through the pumping chamber is dependent upon temperature. For the hyperpolarization of $^{129}$Xe (3% in 96% helium; 10 atm) in this 30 cm$^3$ chamber, the flow rate can be in the range of from about 300 cm$^3$/min to about 600 cm$^3$/min at 150° C. Modeling indicates that from about 20% to about 30% of the laser light is absorbed at 150° C., corresponding to a spin exchange time ($\tau_{SE}$) of 22 s, and an average rubidium polarization of about 50%.

EXAMPLE 2

A gas mixture of 3% Xe having a natural isotopic composition of about 26% $^{129}$Xe, 1% nitrogen, and 96% helium was polarized using the apparatus described in Example 1. In addition, a cryotrapping accumulator according to the invention was used to accumulate the gas leaving the pumping chamber. Using liquid nitrogen as a refrigerant for a glass cold finger, 120 cm$^3$ of frozen hyperpolarized $^{129}$Xe was accumulated in 0.5 hr. The nominal flow rate of the target gas during accumulation was 80–100 cm$^3$/min at STP. Since the gas mixture was only 3% Xe, this permitted a xenon accumulation rate of up to about 3 cm$^3$/min at STP. Upon subliming, the $^{129}$Xe was allowed to expand back into the pumping chamber, which was equipped with a pulsed NMR coil. The NMR signal strength was determined to be about ¼ of the largest saturation even seen from the He:Xe:N$_2$ gas mixture in a sealed pump chamber. From computer modeling, it is believed that the saturation polarization of $^{129}$Xe during an optical pumping procedure is about 75%. The pressure of the sublimed xenon was measured with a capacitance manometer to be 1.21 atm compared to 0.27 atm of xenon in the gas mixture during pumping. Given the ratio of pressures and NMR signals, we arrived at a rough polarization of the accumulated $^{129}$Xe of 5%.

The net polarization obtained in this experiment was within an order of magnitude of the theoretical maximum polarization. Thus, while it must be recognized that this procedure was not optimized, it is shown that the continuous production of hyperpolarized $^{129}$Xe is possible using the method and apparatus of the invention. Moreover, the production and accumulation process preserved a significant amount of the polarization of the xenon. Based on this study, we expect improvements in yield for the sublimed gas.

A significant feature of the method and apparatus of the invention is that substantially larger amounts of hyperpolarized xenon can now be produced than were possible using substantially pure xenon as a target gas. That is, the yield of hyperpolarized xenon as a function of time is substantially increased, notwithstanding the fact that the xenon is present as only a small fraction when the target gas is 90% or more of a buffer gas.

Clearly, the volumes of hyperpolarized $^{129}$Xe obtained using the apparatus of the invention permit the generation of volumes of hyperpolarized noble gases on the order of at least tens of liters per day. Accordingly, the invention now enables, for the first time, the production of sufficient polarized noble gases to enable clinical ventilation studies of human lung by MRI.

Thus, while there have been described what are presently believed to be the preferred embodiments of the present invention, those skilled in the art will realize that other and further embodiments can be made without departing from the spirit of the invention, and it is intended to include all such further modifications and changes as come within the true scope of the claims set forth herein.

What is claimed is:

1. A method for hyperpolarizing a flowing noble gas, comprising:
   a) flowing a target gas, comprising a noble gas, through a pumping chamber; and
   b) hyperpolarizing said flowing noble gas in said pumping chamber by spin exchange with alkali metal atoms, to provide a flowing hyperpolarized noble gas.

2. A method according to claim 1, wherein said flowing comprises flowing said target gas through said pumping chamber at a rate which provides an average atom residence time of said noble gas of from about 0.5 to about 5 times the spin exchange time $\tau_{SE}$ between atoms of the alkali metal and the noble gas.

3. A method according to claim 2, wherein said flowing comprises flowing said target gas through said pumping chamber at a rate which provides an average atom residence time of said noble gas of from about 1 to about 3 times the spin exchange time $\tau_{SE}$ between atoms of the alkali metal and the noble gas.

4. A method according to claim 1, wherein said flowing comprises continuously flowing said target gas through said polarization chamber during said hyperpolarizing of said noble gas.

5. A method according to claim 1, further comprising temporarily isolating a quantity of said target gas in said pumping chamber to permit hyperpolarizing of a quantity of said noble gas.

6. A method according to claim 5, wherein said method is performed at least twice, to provide two or more quantities of said hyperpolarized noble gas.

7. A method according to claim 1, wherein said alkali metal atoms are selected from the group consisting of rubidium, cesium, and potassium atoms.

8. A method according to claim 1, wherein said noble gas is xenon, comprising $^{129}$Xe in at least natural isotopic abundance.

9. A method according to claim 8, wherein said noble gas is xenon comprising a proportion of $^{129}$Xe substantially greater than the natural isotopic abundance of $^{129}$Xe.

10. A method according to claim 1, wherein said noble gas is helium comprising a proportion of $^3$He substantially greater than the natural isotopic abundance of $^3$He.

11. A method according to claim 1, wherein said target gas further comprises a quenching gas for quenching alkali-metal fluorescence during said hyperpolarizing.

12. A method according to claim 11, wherein said quenching gas is nitrogen or hydrogen.

13. A method according to claim 11, wherein said noble gas comprises $^{129}$Xe, and said target gas further comprises a buffer gas which causes pressure broadening of the optical absorption spectrum of said alkali metal atoms.

14. A method according to claim 13, wherein said buffer gas and said quenching gas are different.

15. A method according to claim 11, wherein said buffer gas is helium or hydrogen.

16. A method according to claim 11, wherein said target gas comprises from about 0.1% to about 5% $^{129}$Xe, from about 0.1% to about 30% of a quenching gas, with the balance being helium.

17. A method according to claim 16, wherein said target gas comprises about 1% $^{129}$Xe, about 1% nitrogen, with the balance being helium.

18. A method according to claim 11, wherein said target gas comprises from about 0.1% to about 5% $^{129}$Xe, with the balance being hydrogen.

19. A method according to claim 1, wherein said procedure further comprises accumulating said hyperpolarized noble gas.

20. A method according to claim 19, wherein said noble gas comprises $^{129}$Xe, and said accumulating includes accumulating said $^{129}$Xe in a frozen state.

21. A method according to claim 1, comprising flowing said target gas under hyperbaric conditions.

22. A method according to claim 21, wherein said hyperbaric conditions comprise a pressure of from about 1 atm to about 30 atm.

23. A method according to claim 1, wherein said flowing further comprises removing impurities capable of interfering with the hyperpolarizing from said flowing target gas prior to entry of the target gas into the pumping chamber.

24. A method according to claim 1, wherein said hyperpolarizing includes heating said pumping chamber to heat said flowing target gas during hyperpolarizing.

25. A method for hyperpolarizing $^{129}$Xe, comprising: hyperpolarizing $^{129}$Xe in a target gas, wherein said target gas comprises:

a) a fluorescence-quenching gas, for quenching alkali-metal fluorescence, b) a buffer gas, for pressure-broadening the optical absorption spectrum of alkali metal atoms, and c) xenon comprising $^{129}$Xe in at least natural isotopic abundance;

under conditions sufficient to induce hyperpolarization of said $^{129}$Xe by spin exchange with alkali metal atoms, thereby providing hyperpolarized $^{129}$Xe.

26. A method according to claim 25, wherein said quenching gas and said buffer gas are different.

27. A method according to claim 25, wherein said quenching gas is nitrogen or hydrogen.

28. A method according to claim 25, wherein said buffer gas is helium or hydrogen.

29. A method according to claim 25, wherein said hyperpolarizing comprises flowing said target gas during said hyperpolarizing.

30. A method according to claim 25, wherein said target gas comprises from about 0.1% to about 5% $^{129}$Xe, from about 0.1% to about 30% of said quenching gas, with the balance being helium.

31. A method according to claim 30, wherein said target gas comprises about 1% $^{129}$Xe, about 1% nitrogen, with the balance being helium.

32. Apparatus for hyperpolarizing a noble gas, comprising:

a) a target gas delivery system adapted to deliver a flowing target gas comprising a noble gas;

b) a pumping chamber for hyperpolarizing flowing noble gas by spin exchange with optically pumped alkali metal atoms; and c) hyperpolarization means for hyperpolarizing said flowing noble gas in said pumping chamber.

33. Apparatus according to claim 32, wherein said target gas delivery system comprises a gas container capable of maintaining said target gas under compression.

34. Apparatus according to claim 32, wherein said target gas delivery system further comprises target gas purifying means for removing impurities capable of interfering with said hyperpolarizing from said target gas prior to flow of the target gas through said pumping chamber.

35. Apparatus according to claim 32, wherein said apparatus further comprises a receiving reservoir adapted to receive hyperpolarized noble gas flowing from said pumping chamber.

36. Apparatus according to claim 35, wherein said receiving reservoir comprises a cryotrapping accumulator for accumulating $^{129}$Xe in a frozen state.

37. Apparatus according to claim 32, wherein said apparatus is adapted to permit flowing of said target gas through said pumping chamber during hyperpolarizing.

38. Apparatus according to claim 32, wherein said apparatus is adapted to permit controllable isolation of a quantity of said flowing noble gas in said pumping chamber during hyperpolarizing.

39. Apparatus according to claim 32, wherein said apparatus is adapted to deliver said target gas through said pumping chamber at a rate sufficient to provide an average atom residence time of said noble gas in said pumping chamber of from about 0.5 to about 5 times the spin exchange time $\tau_{SE}$ between atoms of the alkali metal and the noble gas.

40. Apparatus according to claim 39, wherein said apparatus is adapted to deliver said target gas through said pumping chamber at a rate sufficient to provide an average atom residence time of said noble gas in said pumping chamber of from about 1 to about 3 times the spin exchange time $\tau_{SE}$ between atoms of the alkali metal and the noble gas.

41. Apparatus according to claim 32, wherein said hyperpolarizing means comprises a laser system which is capable of delivering hyperpolarizing radiation into said pumping chamber in an amount sufficient for hyperpolarizing a noble gas by spin exchange with alkali metal atoms.

42. Apparatus according to claim 41, wherein said laser system comprises at least one laser source capable of delivering hyperpolarizing radiation in an amount sufficient for hyperpolarizing said noble gas via spin exchange with rubidium, cesium, or potassium atoms.

43. Apparatus according to claim 42, wherein each of said laser sources comprises a laser diode array.

44. Apparatus according to claim 43, wherein said laser diode array is a two-dimensional laser diode array.

45. Apparatus according to claim 41, wherein said laser system comprises two laser sources in opposing arrangement along a single optical axis, with said pumping chamber adapted to admit radiation from both laser sources.

46. Apparatus according to claim 41, wherein said hyperpolarizing means further includes radiation focusing means for focusing radiation emitted from said laser system into said pumping chamber.

47. Apparatus according to claim 46, wherein said focusing means comprises a Fresnel lens.

48. Apparatus according to claim 32, wherein said pumping chamber is cylindrical, conical, or frustoconical.

49. Apparatus according to claim 32, further comprising heating means for heating said pumping chamber.

50. Apparatus according to claim 32, further comprising means for monitoring hyperpolarization.

51. Apparatus according to claim 50, wherein said hyperpolarization monitoring means comprises means for performing NMR polarimetry.

52. Apparatus according to claim 32, wherein said pumping chamber further comprises a fluorescence observation window.

53. Apparatus according to claim 52, further comprising fluorescence monitoring means for monitoring fluorescence through said fluorescence observation window.

54. Apparatus according to claim 32, wherein said apparatus is operable using said noble gas under hyperbaric conditions.

55. Apparatus according to claim 54, wherein said apparatus is operable using a gas pressure of from about 1 atm to about 30 atm.

56. Apparatus according to claim 32, wherein said apparatus contains an amount of an alkali metal sufficient to permit maintenance of adequate alkali-metal vapor density during a hyperpolarization procedure.

57. Apparatus according to claim 32, further comprising an alkali-metal vaporizer to provide alkali-metal vapor to said pumping chamber during hyperpolarizing.

58. Apparatus according to claim 32, further comprising alkali-metal refluxing means for recovering alkali-metal vapor from said flowing target gas exiting said pumping chamber.

59. Apparatus according to claim 32, further comprising alkali-metal recirculating means for recirculating alkali metal through said pumping chamber during hyperpolarizing.

60. Apparatus for hyperpolarizing flowing $^3$He, comprising:

a) hyperpolarization means, comprising:
  1) a laser system capable of delivering hyperpolarizing radiation sufficient to hyperpolarize $^3$He by spin exchange with alkali metal atoms, and
  2) a computer system enabling control and monitoring of a hyperpolarization procedure; and
b) a replaceable polarization unit, comprising:
  1) a target gas delivery system for maintaining and delivering a target gas comprising $^3$He at a hyperbaric pressure, and
  2) a pumping chamber in fluid communication with said target gas delivery system;

wherein said replaceable polarization unit engages and is operable with said hyperpolarization means so that the pumping chamber is oriented to admit hyperpolarizing radiation from said laser source into said pumping chamber for hyperpolarization of said $^3$He.

61. Apparatus for use in hyperpolarizing $^3$He, comprising:
  a removable polarization unit comprising:
    a pumping chamber adapted to permit flow-through of a target gas comprising $^3$He, and permissive to hyperpolarizing radiation sufficient to hyperpolarize $^3$He by spin exchange with alkali metal atoms, wherein said polarization unit is adapted to removably engage a hyperpolarizing system comprising a laser system capable of delivering hyperpolarizing radiation into said pumping chamber when said polarization unit is engaged therewith.

62. Apparatus for hyperpolarizing $^3$He, comprising:
  a hyperpolarizing system comprising:
    a laser system for delivering hyperpolarizing radiation sufficient to enable hyperpolarization of $^3$He by spin exchange with alkali metal atoms;

wherein said hyperpolarizing system is adapted to removably engage a replaceable polarization unit having a pumping chamber adapted to permit flow-through of a target gas comprising $^3$He, and is capable of delivering hyperpolarizing radiation into said pumping chamber when said polarization unit is engaged therewith.

* * * * *

UNITED STATES PATENT AND TRADEMARK OFFICE
CERTIFICATE OF CORRECTION

PATENT NO. : 5,642,625
DATED : July 1, 1997
INVENTOR(S) : Cates, Jr. et al.

Page 1 of 2

It is certified that error appears in the above-indentified patent and that said Letters Patent is hereby corrected as shown below:

<u>In Column 1, Line 6,</u>   the patent now reads "may have fights in"; this should read --may have rights in--.

<u>In Column 5, Line 1,</u>   the patent now reads "includes a minor mount"; this should read --includes a minor amount--.

<u>In Column 15, Line 33,</u>   the patent now reads "absorption oft he hyperpolarizing"; this should read --absorption of the hyperpolarizing--.

<u>In Column 16, Line 37,</u>   the patent now reads "has separate reseatable inlet"; this should read --has separate resealable inlet--.

<u>In Column 16, Line 62,</u>   the patent now reads "valves in the reseatable gas"; this should read --valves in the resealable gas--.

UNITED STATES PATENT AND TRADEMARK OFFICE
CERTIFICATE OF CORRECTION

PATENT NO. : 5,642,625
DATED : July 1, 1997
INVENTOR(S) : Cates, Jr. et al.

It is certified that error appears in the above-indentified patent and that said Letters Patent is hereby corrected as shown below:

In Column 20, Line 32,   the patent now reads "in a preheated embodiment"; this should read --in a preferred embodiment--.

In Column 21, Line 2,   the patent now reads "few tens of arm), which"; this should read --few tens of atm), which--.

In Column 22, Line 2,   the patent now reads "and being carded into the"; this should read --and being carried into the--.

In Column 22, Line 20,   the patent now reads "part of a timed circuit which"; this should read --part of a tuned circuit which--.

In Column 26, Line 58,   the patent now reads "solid (T<160K) solves"; this should read --solid (T≤ 160K) solves--.

Signed and Sealed this

Fourteenth Day of October, 1997

Attest:

BRUCE LEHMAN

*Attesting Officer*   Commissioner of Patents and Trademarks